US008802660B2

(12) United States Patent
Tomic-Canic et al.

(10) Patent No.: US 8,802,660 B2
(45) Date of Patent: Aug. 12, 2014

(54) DE NOVO SYNTHESIS OF GLUCOCORTICOIDS IN THE EPIDERMIS AND ITS USES AND APPLICATIONS

(75) Inventors: Marjana Tomic-Canic, Miami, FL (US); Harold Brem, Bronx, NY (US); Herbert H. Samuels, New Rochelle, NY (US)

(73) Assignee: New York University, New York, NY (US)

( * ) Notice: Subject to any disclaimer, the term of this patent is extended or adjusted under 35 U.S.C. 154(b) by 525 days.

(21) Appl. No.: 12/075,672

(22) Filed: Mar. 12, 2008

(65) Prior Publication Data

US 2008/0274079 A1 Nov. 6, 2008

Related U.S. Application Data

(60) Provisional application No. 60/894,383, filed on Mar. 12, 2007.

(51) Int. Cl.
*A01N 45/00* (2006.01)
*A61K 31/56* (2006.01)

(52) U.S. Cl.
USPC ........................................ 514/169; 514/178

(58) Field of Classification Search
USPC ................................. 514/169, 178
See application file for complete search history.

(56) References Cited

FOREIGN PATENT DOCUMENTS

WO  WO 2004/112779  * 12/2004
WO  WO2004/112779  * 12/2004

OTHER PUBLICATIONS

Kumar et. al. (J. Steroid. Biochem. Molec. Biol. (1997) 62:195-199).*
Kagawa et. al. (Zoological science (2002) 19:735-740).*
Slominski et. al. (FEBS Letters (1995) 374:113-116).*
Dempsey, Annual review of Biochemistry (1974) 43:967-990.*
Curnow et. al., Current Opinion in Endocrinology and Diabetes (1994) 10-15.*
Oishi et al., "Molecular basis of the alteration in skin collagen metabolism in response to in vivo dexamethasone treatment: effects on the synthesis of collagen type I and III, collagenase, and tissue inhibitors of metalloproteinases," (2002) British Journal of Dermatology, 147:859-868.
Madlener et al., "Matrix Metalloproteinases (MMPs) and Their Physiological Inhibitors (TIMPs) are Differentially Expressed during Excisional Skin Wound Repair," (1998) Experimental Cell Research, 242:201-210.
Tsigos et al., "Hypothalamic-pituitary-adrenal axis, neuroendocrine factors and stress," (2002) Journal of Psychosomatic Research, 53:856-871.
Quinkler et al., "Hypertension and the Cortisol-Cortisone Shuttle", (2003) J. Clin. Endocrinol. Metab. 88 (6):2384-92.

Albiston et al., "Cloning and tissue distribution of the human 11β-hydroxysteroid dehydrogenase type 2 enzyme", (1994) Mol. Cell. Endicrinol. 105: R11-R17.
Hardy et al., "Differential expression, function and response to inflammatory stimuli of 11β-hydroxysteroid dehydrogenase type 1 in human fibroblasts: a mechanism for tissue-specific regulation of inflammation", (2006) Arthritis Res. Ther. 8: R108.
Zoubolis et al., "Human Skin: An Independent Peripheral Endocrine Organ", (2000) Hormone Res. 54:230-242.
Ermak et al., "Production of POMC, CRH-R1, MC1, and MC2 Receptor mRNA and Expression of Tyrosinase Gene in Relation to Hair Cycle and Dexamethasone Treatment in the C57BL/6 Mouse Skin", (1997) J. Invest. Dermatol. 108:160-165.
Slominski et al., "Proopiomelanocortin, corticotropin releasing hormone and corticotropin releasing hormone receptor genes are expressed in human skin", (1995) FEBS Letters 374: 113-116.
Ito et al., "Human haur fikkuckes dusokay a functional equivalent of the hypothalamic-pituitary-adrenal axis and synthesize cortisol", (2005) FASEB 19(1)1332-34.
Slominski et al, "Cultured Human Dermal Fibroblasts do Produce Cortisol", (2006) J. Invest. Dermatoi. 126(5): 1177-1178.
Slominski et al., "CRH stimulation of corticosteroids production in melanocytes is mediated by ACTH", (2005) J. Physiol. Endocrinoi. Metebol. 288(4):E701-06.
Brem et al., "Healing of Elderly Patients with Diabetic Foot Ulcers, Venous Stasis Ulcers, and Pressure Ulcers", (2003) Surg. Tech. Int. 11: 161-167.
Williams et al., "Effect of sharp debridement using curette on recalcitrant nonhealing venous leg ulcers: A concurrently controlled, prospective cohort study", (2005) Wound Repair Regen. 13: 131-137.
Steed et al., "Effect of Extensive Debridement and Treatment of the Healing of Diabetic Foot Ulcers", (1996) J. Amer. Coli. Surg. 183(1): 61-64.
Jho et al., "Negative Response Elements in Keratin Genes Mediate Transcriptional Repression and the Cross-talk among Nuclear Receptors", (2001) J. Biol. Chern. 276 (49):45914-45920.
Radoja et al., "Novel Mechanism of Steroid Action in Skin through Glucocorticoid Receptor Monomers", (2000) Mol. Cell. Biol. 20:4328-4339.
Stojadinovic et al., "Molecular Pathogenesis of Chronic Wounds: The Role of β-Catenin and c-myc in the Inhibition of Epithelialization and Wound Healing", (2005) Am. J. Pathol. 167(1):56-69.
Lee et al., "From an Enhanceosome to a Repressosome: Molecular Antagonism between Glucocorticoids and EGF Leads to Inhibition of Wound Healing", (2005) J. Mol. Biol. 345(5): 1083-97.
Morasso and Tomic-Canic et al., "Epidermal stem cells: the cradle of epidermal determination, differentiation and wound healing," (2005) Biol. Cell 97(3): 173-183.

(Continued)

*Primary Examiner* — Marcos Sznaidman
(74) *Attorney, Agent, or Firm* — Troutman Sanders LLP

(57) ABSTRACT

The present invention relates to methods and compositions that control, i.e., antagonize/inhibit or agonize/stimulate, de novo glucocorticoid production in the skin. Such methods and compositions can be used for the prevention and/or treatment of a variety of skin conditions, including inflammation, acute wounds, chronic non-healing wounds, keloid, fibrotic or hypertrophic scars, and epithelial-derived cancer.

4 Claims, 15 Drawing Sheets
(10 of 15 Drawing Sheet(s) Filed in Color)

(56) References Cited

OTHER PUBLICATIONS

Li et al., "Extensive tissue-regenerative capacity of neonatal human keratinocyte stem cells and their progeny," (2004) J.Clin. Invest 113(3):390-400.
Johnston et al., "Targeting the EGFR Pathway for Cancer Therapy", (2006) Curro Med. Chem. 13(29):3483-3492.
Rosen et al., "A Primary Protocol for the Management of Ear Keloids: Results of Excision Combined with Intraoperative and Postoperatie Steroid Injections," (2007) Plast. Reoonstr. Surg. 120: 1395-4000.
Jalali et al., "Current use of steroids in management of abnormal raised skin scars", (2007) Surgeon 5:175-80.
Wu et al., "Dexamethasone Induction of Keloid Regression through Effective Suppression of VEGF Expression and Keloid Fibroblast Proliferation", (2006) J. Invest. Dermatol. 126:1264-1271.
Tang et al., "Intra- and postoperative steroid injections for keloids and hypertrophic scars", (1992) Brit. J. Plastic Surg. 45:371-373.
Tomic-Canic et al., "Streptolysin O enhances keratinocyte migration and proliferation and promotes skin organ culture wound healing in vitro", (2007) Wound Repair Regen. 15(1):71-79.
Chabre et al., "Bilateral Laparoscopic Adrenalectomy for Congenital Adrenal Hyperplasia with Severe Hypertension, Resulting from Two Novel Mutations in Splice Donor Sites of CYP11B1," (2000) J. Clin. Endo. and Metabol. 85:4060-4068.
Ismaili et al., "Modulation of Glucocorticoid Receptor Function via Phosphorylation" (2004) Annals of NY Acad. Science 1024:86-101.
Wang and Garanedian et al., "Modulation of Glucocorticoid Receptor Transcriptional Activation, Phosphorylation, and Growth Inhibition by p27Kipl," (2003) J. Bioi. Chem. 278(51):50897-901.
Randolph and Simon et al., "Characterization of Retinol Metabolism in Cultured Human Epidermal Keratinocytes," (1993) J. Biol. Chem. 268(13):9198-9205.
Rappolee et al., "Wound Macrophages Express TGF-$\alpha $ and other Growth Factors in vivo: Analysis by mRNA Phenotyping", (1988) Science 241:708-12.
Horiuchi et al., "Pro-inflammatory cytokine IL-1α potential for tissue repair in chemically and mechanically induced injury in cultured human keratinocytes" (2004) J. Dermatol. Science 35:224-6.
Iglesias et al., "Human papillomavirus type 16 E7 protein sensitizes cervical keratinocytes to apoptosis and release of interleukin-1α," (1998) Oncogene 17:1195-205.
Freedberg at al., "Keratins and the Keratinocyte Activation Cycle", (2001) J. Invest. Dermatol. 116:633-640.
Tomic-Canic at al., "Epidermal signal transduction and transcription factor activation in keratinocytes" (1998) J. Dermatol. Science 17(3): 167-181.
Kupper et al., "The Activated Keratinocyte: A Model for Inducible Cytokine Production by Non-Bone Marrow-Derived Cells in Cutaneous Inglammatory and Immune Responses", (1990) J. Invest. Dennatol. 94: 146S-150S.
Stojadinovic et al., "Novel Genomic Effects of Glucocorticoids in Epidermal Keratinocytes", (2007) J. Biol. Chem. 282:4021-34.

Quinkler, M., and Stewart, P. M. "Hypertension and the Cortisol-Cortisone Shuttle" J. Clin. Endocrinol. Metab. vol. 88, pp. 2384-2392 (2003).
Tomlinson et al. "11β-Hydroxysteriod Dehydrogenase Type 1: A Tissue-Specific Regulator of Glucocorticoid Response," Endocrine Reviews (2004) 25(5):831-866—36 pages.
Taves et al. "Extra-adrenal glucocorticoids and mineralocorticoids: evidence for local synthesis, regulation, and function," (Am J Physiol Endocrinol Metab) (2011) 301: E11-E24—15 pages.
Bureik, et al., "Development of test systems for the discovery of selective human aldosterone synthase (CYP11B2) and 11β-hydroxylase (CYP11B1) inhibitors. Discovery of a new lead compound for the therapy of congestive heart failure, myocardial fibrosis and hypertension", Molecular and Cellular Endocrinology, vol. 217, pp. 249-254, 2004.
Johansson, et al., "Structure-Activity Relationship for Inhibition of CYP11B1—Dependent Glucocorticoid Synthesis in Yl Cells by Aryl Methyl Sulfones", Pharmacology & Toxicology, vol. 83, pp. 225-230, 1998.
Johansson, et al., "Effects of 3-MeSO$_2$-DDE and some CYP inhibitors on glucocorticoid steroidogenesis in the H295R human adrenocortical carcinoma cell line", Toxicology in Vitro, vol. 16, pp. 113-121, 2002.
Hakki and Bernhardt, "CYP17- and CYP11B-dependent steroid hydroxylases as drug development targets", Pharmacology & Therapeutics, vol. 111, pp 27-52, 2006.
Slight, et al., Inhibition of tissue repair by spironolactone: Role of mineralocorticoids in fibrous tissue formation, Molecular and Cellular Biochemistry, vol. 189, pp. 47-54, 1998.
Gambineri, et al., Genetic Variation in 11β-Hydroxysteroid Dehydrogenase Type 1 Predicts Adrenal Hyperandrogenism among Lean Women with Polycystic Ovary Syndrome, The Journal of Clinical Endocrinology & Metabolism, vol. 91, pp. 2295-2302, 2006.
Malunowicz, et al., 11β-Hydroxysteroid Dehydrogenase Type 1 Deficiency ('Apparent Cortisone Reductase Deficiency') in a 6-Year-Old Boy, Hormone Research, vol. 59, pp. 205-210, 2003.
Friedberg, et al., Modulation of 11β-Hydroxysteroid Dehydrogenase Type 1 in Mature Human Subcutaneous Adipocytes by Hypothalamic Messengers, The Journal of Clinical Endocrinology & Metabolism, vol. 88, pp. 385-393, 2003.
Slominski, et al., Differential expression of hpa axis homolog in the skin, Mol Cell Endocrinol, vol. 265-266, pp. 143-149, 2007.
Slominski, et al., Cutaneous Expression of CRH and CRH-R is There a "Skin Stress Response System?", Ann NY Acad Sci., vol. 885, pp. 287-311, 1999.
Andersen, C.Y., Possible new mechanism of cortisol action in female reproductive organs: physiological implications of the free hormone hypothesis, Journal of Endocrinology, vol. 173, pp. 211-217, 2002.
Hardy, et al., Differential expression, function and response to inflammatory stimuli of 11β-hydroxysteroid dehydrogenase type 1 in human fibroblasts: a mechanism for tissue-specific regulation of inflammation, Arthritis Res Ther., vol. 8, p. R108, 2006.

* cited by examiner

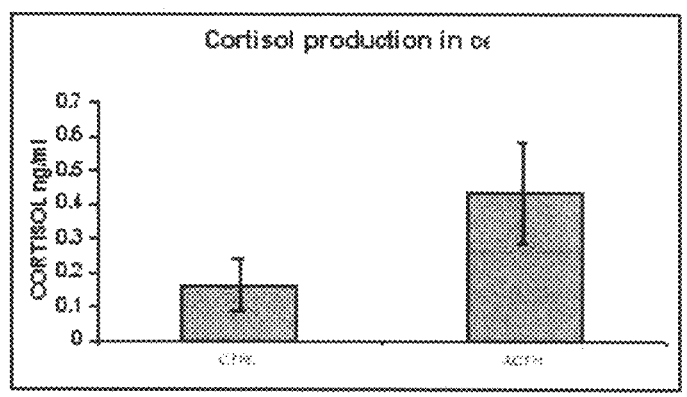
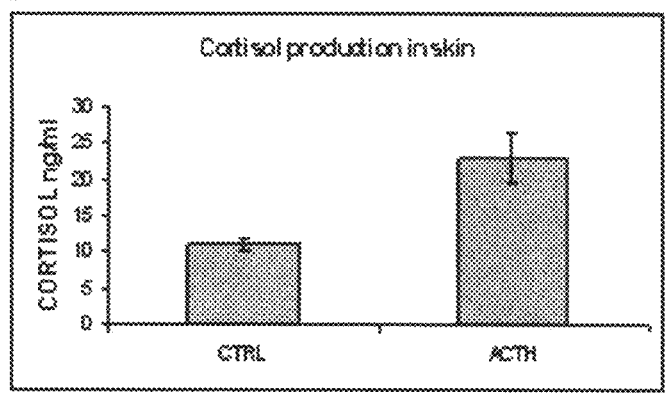
Figure 3

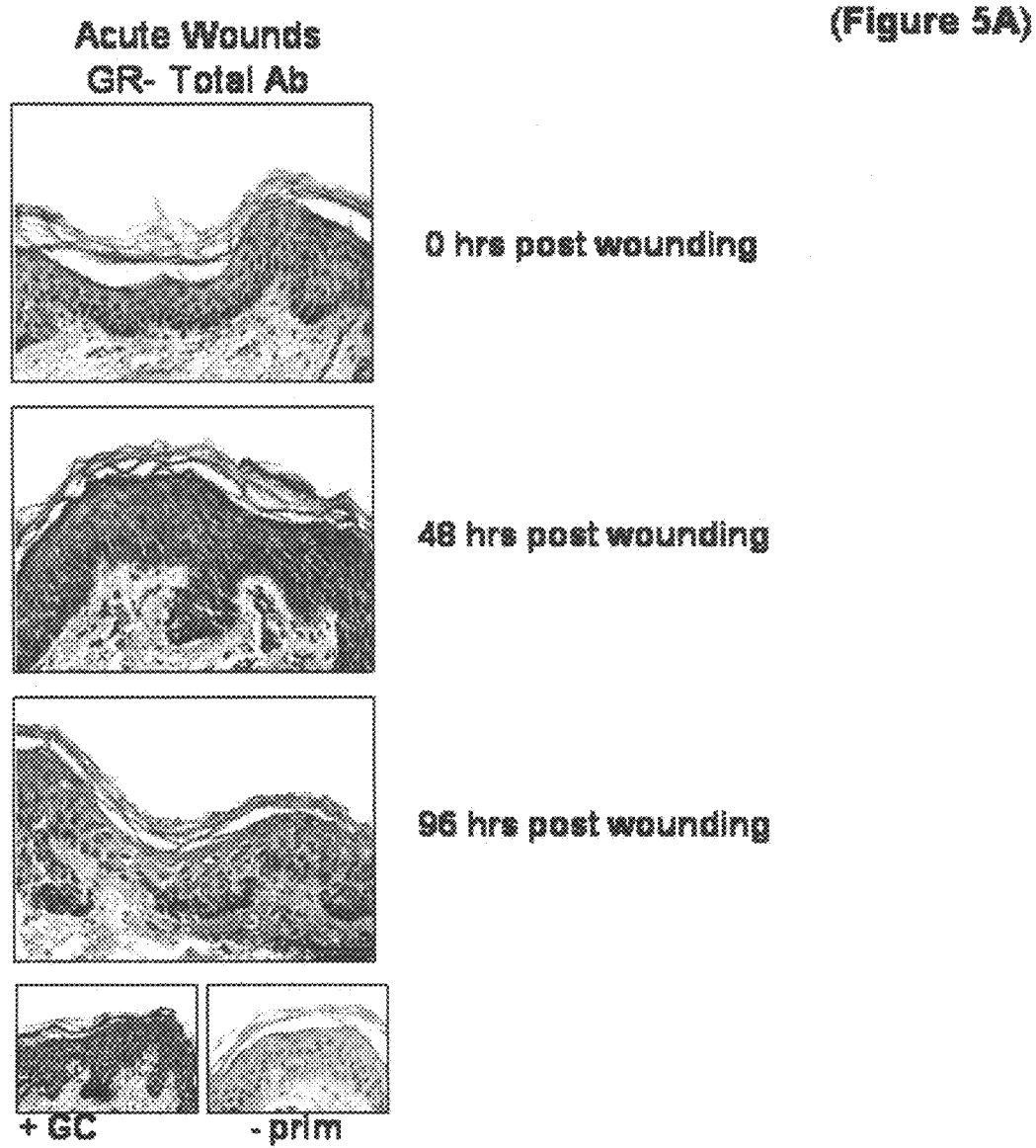
(Figure 5A)

(Figure 5B)
Acute Wounds
GR- Phosphorylated Ab
0 hrs post wounding
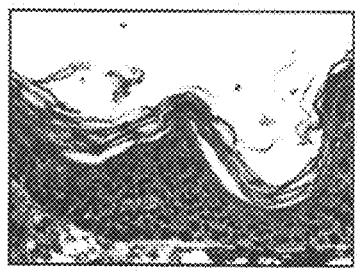
48 hrs post wounding
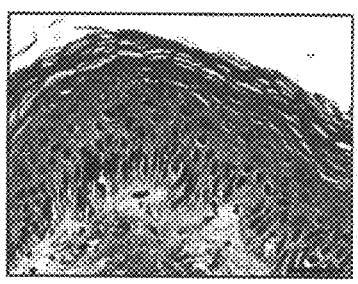
96 hrs post wounding
 
+ GC      - Prim Ab A.
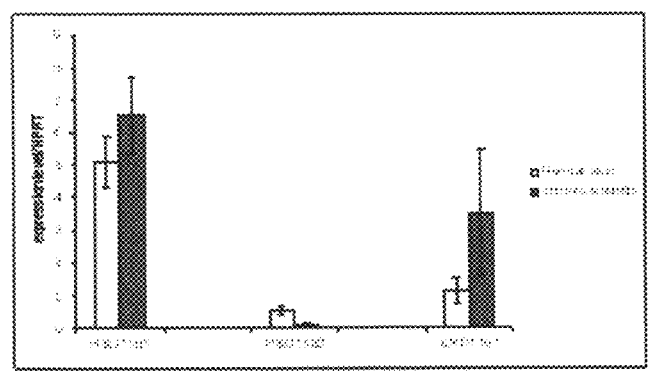
(Figure 6)
B. Chronic Wound Biopsy
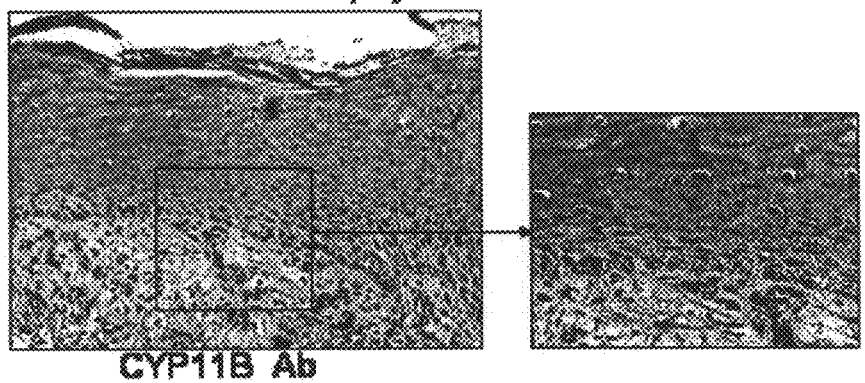
CYP11B Ab
C.
Chronic Wound Biopsy
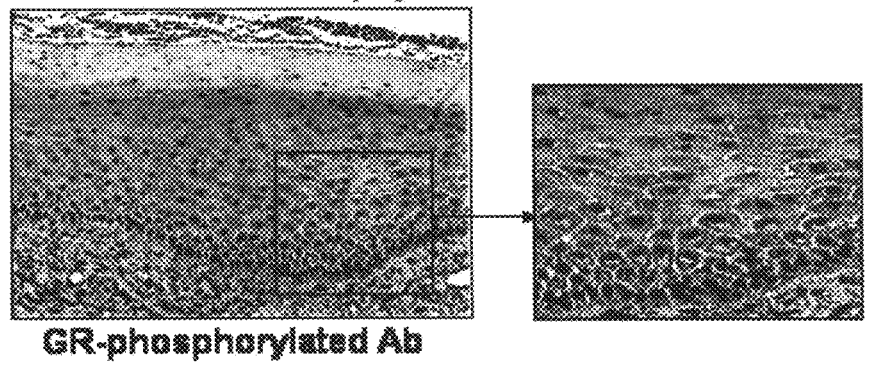
GR-phosphorylated Ab

DE NOVO SYNTHESIS OF GLUCOCORTICOIDS IN THE EPIDERMIS AND ITS USES AND APPLICATIONS

CROSS-REFERENCE TO RELATED APPLICATIONS

This application claims priority to U.S. Provisional Application Ser. No. 60/894,383, filed Mar. 12, 2007, which is incorporated by reference herein in its entirety.

FIELD OF THE INVENTION

The present invention relates to discovery that epidermis produces glucocorticoid de novo. Methods and compositions that control, i.e., antagonize/inhibit or agonize/stimulate, this de novo glucocortoicoid production can be used for the prevention and treatment of a variety of skin conditions, including inflammation, acute wounds, chronic non-healing wounds, keloids or hypertrophic scars, and epithelial-derived cancer.

BACKGROUND OF THE INVENTION

Glucocorticoids (GC) are known inhibitors of wound healing, suppressing many wound healing regulators, such as IL-1, TNFα, KGF, PDGF, FGF, MME and collagens (Oishi et al. (2002) *Brit. J. Dermatol.* 147:859-68; Madlener et al. (1998) *Exp. Cell Res.* 242:201-10). Glucocorticoids affect all of the essential steps of normal wound healing, including the early inflammatory phase, matrix deposition, and angiogenesis.

The hypothalamic-pituitary-adrenal (HPA) axis is responsible for the production of steroid hormones with glucocorticoid activity. The hypothalamus controls the secretion of ACTH from the pituitary gland, which in turn, stimulates the secretion of cortisol by the adrenal gland (Tsigos et al. (2002) *J. Psychosomatic Res.* 53:856-871).

In humans, cortisol is the most important steroid hormone with glucocorticoid activity. Adults secrete about 20 μg of cortisol daily in a pronounced circadian cycle. Plasma levels of cortisol vary from 5-25 μg/dL, but only a fraction of this hormone is physiologically active as more than 95% of circulating plasma cortisol is bound reversibly to circulating plasma proteins.

Glucocorticoid shares a synthesis pathway with aldosterone and androgens in the adrenal gland proceeding up until the final step. The final step specific for glucocorticoids involves the steroid 11 beta-hydroxylase (CYP11B), a mitochondrial chytochrome P-450. An additional fine-tuning mechanism in the cortisol pathway involves 11β-hydroxysteroid dehydrogenase (11β-HSD) HSD11B1/HSD11B2 enzymes. These two distinct isozymes of 11β-HSD catalyze the interconversion of hormonally active cortisol and inactive cortisone. HSD11B1 converts inactive cortisone to active cortisol. HSD11B2 converts active cortisol to the inactive form of cortisone, thus preventing cortisol binding to the receptor (Quinkler et al. (2003) *J. Clin. Endocrinol. Metab.* 88(6):2384-92; Albiston et al. (1994) *Mol. Cell. Endocrinol.* 105:R11-R17). Recent data suggests that tissue-specific regulation of GCs, mediated via differential regulation of the enzyme HSD11B1, can play an important role in defining tissue-specific responses during the resolution of inflammation (Hardy et al. (2006) *Arthritis Res. Ther.* 8:R108).

Very little is known about steroidegenesis in non-adrenal tissue. However, the concept of skin as an endocrine organ is not new (Zouboulis (2000) *Hormone Res.* 54:230-242). Skin expresses most hormone receptors, and is able to metabolize, activate, and inactivate hormones. Epidermal cells have been implicated in the production of endogenous hormones equivalent to the HPA axis, including corticotrophin releasing hormone (CRH) and the proopiomelanocortin (POMC) derived peptides, MSH, adrenocorticotropic hormone (ACTH), and β-endorphin. (Ermak et al. (1997) *J. Invest. Dermatol.* 108:160-165; Slominski et al. (1995) *FEBS Letters* 374:113-116). Furthermore, isolated hair follicles secrete substantial levels of cortisol and display HPA axis-like regulatory feedback systems (Ito et al. (2005) *FASEB* 19(1)1332-34). It has also been shown that fibroblasts and melanocytes produce cortisol in vitro (Slominski et al. 2006) *J. Invest. Dermatol.* 126(5):1177-8; Slominski et al. (2005) *J. Physiol. Endocrinol. Metabol.* 288(4):E701-06).

Glucocorticoid activates the glucocorticoid receptor (GR) pathway. Upon activation, the GR, bound to the glucocorticoid, translocates from the cytoplasm of the cell to the nucleus. The GR pathway is found in many types of cells, including epidermis. The GR is involved, at least, in the NF-kB pathway and may decrease inflammation, in part, by blocking the binding of this transcriptional factor to pro-inflammatory genes.

Non-healing wounds are reaching epidemic proportions among the elderly, the disabled, and those with diabetes (Brem et al. (2003) *Surg. Tech. Int.* 11: 161-167). Chronic ulcers are characterized by physiological impairments, manifested in delays in healing, which results in severe morbidity. Not only do these chronic ulcers significantly impair an affected person's life, the cost of caring for such chronic wounds is burdensome. Over twenty-five billion dollars was spent in the United States alone on the treatment of chronic wounds. (Williams et al. (2005) *Wound Repair Regen.* 13:131-137; Steed et al. (1996) *J. Amer. Coll. Surg.* 77:575-586).

Contributing to the problem of chronic non-healing wounds is the lack of understanding of the molecular mechanisms and the pathogenesis of the impaired healing of such wounds. Until now, the role of glucocorticoids in the development of chronic wounds remained unknown.

SUMMARY OF THE INVENTION

The present invention overcomes problems in the art by elucidating the role of glucocorticoids in the healing of acute wounds and the pathogenesis of chronic non-healing wounds. It has been found, unexpectedly, that epidermis is a steroidogenic tissue, meaning it produces and secretes cortisol de novo. The epidermis produces glucocorticoid in both its healthy state and in an acute wounding state. In both types of tissue, the glucocorticoid receptor pathway is activated and de-activated in an expected pattern. However, it has also been found that glucocorticoid synthesis and the glucocorticoid receptor pathway are erroneously activated in chronic wound tissue. Specifically, chronic wound tissue over-expresses the enzyme, CYP11B, responsible for glucocorticoid synthesis, and the glucocorticoid receptor pathway is activated at all times. These findings have important implications for the prevention and treatment of inflammatory conditions of the skin, acute wounds, and perhaps most importantly, chronic non-healing wounds.

One embodiment of the present invention provides for a method of antagonizing and/or inhibiting glucocorticoid production in the epidermis in a subject in need of such treatment. The method would comprise administering or applying an effective amount of a glucocorticoid antagonist and/or inhibitor in order to antagonize and/or inhibit the production of the glucocorticoid. Such antagonists and/or inhibitors of GC synthesis include RU486 and $CaCl_2$, as well as antagonists and inhibitors of the enzymes that synthesize GC, such as CYP11B. Inhibitors of HSD11B1, which converts cortisone to cortisol, and stimulators of HSD11B2, which converts cortisol to cortisone, could also be used as antagonists and/or inhibitors in this embodiment of the present invention. Such a method would sustain the skins' own pro-inflammatory response, i.e., decrease the anti-inflammatory response.

One reason for antagonizing and/or inhibiting GC production in the epidermis would be to decrease the skins' own anti-inflammatory response in order to effectively administer an exogenous steroid for the treatment of an inflammatory condition and/or an acute wound of the skin, without any interference from an endogenous glucocorticoid. Thus, a further embodiment of the present invention would be to administer or apply the antagonist and/or inhibitor with an exogenous steroid typically used for treating anti-inflammatory conditions of the skin and acute wounds.

Another embodiment of the present invention is a composition for antagonizing and/or inhibiting glucocorticoid production in the epidermis. Such a composition could be applied topically to the skin, and would include the antagonist and/or inhibitor of GC production. RU486, $CaCl_2$, and antagonists of enzymes responsible for GC synthesis (such as CYP11B). Inhibitors of HSD11B1, and stimulators of HSD11B2, could be used as antagonists and/or inhibitors in this embodiment of the present invention. The antagonist/inhibitor could also be in the composition in combination with an exogenous steroid.

Another embodiment of the present invention provides for a method of agonizing and/or stimulating glucocorticoid production in the epidermis in a subject in need of such treatment. The method would comprise administering or applying a glucocorticoid agonist and/or stimulator in an amount effective to agonize and/or stimulate the production of the glucocorticoid. Such agonists and/or stimulators would include agonists and/or stimulators of the enzymes that synthesize GC, such as CYP11B, and enzymes that converts cortisone to cortisol, such as HSD11B1, and inhibitors of enzymes that control production of GC such as HSD11B2. One such inhibitor of HSD11B2 is carbenoxolone (CBX). ACTH is also an agonist/stimulator of GC production. Such a method would sustain the skins' own anti-inflammatory response, i.e., decrease the pro-inflammatory response.

One reason for agonizing and/or stimulating GC production would be to increase the skins' own anti-inflammatory response in order to treat an inflammatory condition of the skin and/or an acute wound. Another indication for agonizing and/or stimulating GC production in epidermis is to inhibit the development and growth of epithelial-derived cancer cells. A further indication would be to treat a keloid, fibrotic or hypertrophic scar.

A further embodiment of the present invention would be to administer or apply the agonist and/or stimulator with an exogenous steroid. The presence of both exogenous steroid and endogenous glucocorticoid would hasten the treatment of an inflammatory condition and/or the healing of an acute wound.

Another embodiment of the present invention is a composition for agonizing and/or stimulating glucocorticoid production in the epidermis. Such a composition could be applied topically to the skin, and would include the agonist and/or stimulator. Agonists and/or stimulators would include agonists of enzymes responsible for GC synthesis and converting cortisone to cortisol, and inhibitors of enzymes responsible for controlling production of GC, i.e., converting cortisol to cortisone. The agonist/stimulator could also be in the composition in combination with an exogenous steroid. Such a composition could be used for the treatment of an anti-inflammatory condition of the skin in a subject in need of such treatment and would be applied in an amount effective to end or decrease the anti-inflammatory condition. This composition of the present invention could also be used for the treatment of acute wounds of the skin in a subject in need of such treatment and would be applied in amount effective to hasten or quicken the healing of the acute wound. This composition of the present invention could also be used for the treatment of keloid, fibrotic or hypertrophic scars of the skin in a subject in need of such treatment, and would be applied in amount effective to induce regression of the scar, and/or prevent the recurrence of the scar. This composition of the present invention could also be used to prevent or treat the development and growth of epithelial-derived cancer cells.

A further embodiment of the present invention is a method for treating and/or preventing chronic non-healing wounds by antagonizing and/or inhibiting glucocorticoid production in the epidermis in a subject in need of such treatment. The method would comprise applying or administering an amount of a glucocorticoid antagonist and/or inhibitor to the affected tissue in an amount effective to antagonize and/or inhibit the production of the glucocorticoid. Such antagonists and/or inhibitors include RU486 and $CaCl_2$, as well as antagonists and inhibitors of the enzymes that synthesis GC, such as CYP11B. Inhibitors of HSD11B1, which converts cortisone to cortisol, and stimulators of HSD11B2, which converts cortisol to cortisone, could also be used as antagonists and/or inhibitors in this embodiment of the present invention. In the case of chronic wounds, the antagonist/inhibitor could be applied to the wound, preferably at the non-healing edge, as soon as it is suspected that the wound is not healing correctly.

Another embodiment of the present invention is a composition for the treatment and/or prevention of chronic non-healing. Such a composition could be applied topically to the skin, and would include the antagonist and/or inhibitor of GC production. RU486, $CaCl_2$, and antagonists of enzymes responsible for GC synthesis and HSD11B1, and stimulators of HSD11B2, could also be used as antagonists and/or inhibitors in this embodiment of the present invention.

A further embodiment of the present invention is a method for determining if chronic non-healing wound tissue has aberrant glucocorticoid production and is in need of treatment with a GC antagonist. One embodiment of this method is performed by obtaining a tissue sample from the chronic non-healing wound, preferably at the non-healing edge, and determining the location of the enzyme CYP11B in the epidermis. This method can be done using any methods known in the art. The preferred method is immunohistology analysis using an antibody to CYP11B. The presence of CYP11B in the suprabasal layer of the epidermis indicates aberrant glucocorticoid production in the tissue. The presence of CYP11B in the basal layer indicates normal glucocorticoid production in the tissue.

Another embodiment of this method is performed by gene and/or protein expression analysis. This method would be performed by obtaining a sample of chronic non-healing tissue and determining the expression of CYP11B and HSD11B2, and comparing the expression to that in normal healthy tissue. The over-expression of CYP11B and under-expression of HSD11B2 as compared to normal skin indicates aberrant production of GC in the non-healing tissue.

Yet another embodiment of the present invention is a method of increasing the effectiveness of an exogenous glucocorticoid treatment, by administering or applying the glucocorticoid with an inhibitor of HSD11B2 or another enzyme that controls the production of GC by converting active cortisol to inactive cortisone. Another embodiment of the present invention is a composition comprising a glucocorticoid and an HSD11B2 inhibitor or the like.

BRIEF DESCRIPTION OF THE DRAWINGS

The file of this patent contains at least one drawing/photograph executed in color. Copies of this patent with color drawing(s)/photograph(s) will be provided by the Office upon request and payment of the necessary fee.

FIG. 1(A) shows the results of immunocytochemical analysis of primary human keratinocytes using a GR-specific antibody and DAPI. FIG. 1(B) shows the results of Western blot analysis of nuclear and cytoplasmic fractions of keratinocytes grown in minimal media for the presence of hormone-activated GR (GR-P). FIG. 1(C) shows the results of immunohistochemistry analysis of normal human skin biopsies stained with GR-specific antibody and GR-specific antibody targeting phosphorylated hormone activated form of the GR, in untreated and glucocorticoid (dexamethasone) treated skin (positive control) and sections stained without primary antibody (negative control).

FIG. 2(A) shows the results of immunohistochemistry analysis of normal human skin using a total CYP11B antibody to determine protein presence and localization. Positive controls were adrenal gland tissue and negative controls were sections stained without primary antibody. FIG. 2(B) shows the results of RT-PCR analysis of primary keratinocytes and human skin biopsies. FIG. 2(C) shows Western blot data of protein extracted from human skin, adrenal gland, epidermis, keratinocytes, fibroblasts, and lymphocytes stained with CYP11B antibody.

FIG. 3 shows the results from ELISA assays for cortisol. Assays were performed on collected medium from primary keratinocytes grown in minimal media with no alternative source of glucocorticoid and from the skin explant cultures. FIG. 3(A) depicts the results of an ELISA assay of cortisol secreted into the medium in ng/ml by epidermal keratinocytes in the presence and absence of ACTH. FIG. 3(B) depicts the results of an ELISA assay of cortisol secreted by the skin explant cultures in the presence and absence of ACTH.

FIG. 5(A) shows the results using immunohistochemistry analysis of acute wounded skin biopsies stained with total GR-specific antibody at 0 hours, 48 hours, and 96 hours post-wounding. Results for the positive control (GC treated skin) and negative control (staining without primary antibody) are also shown. FIG. 5(B) shows the results of immunohistochemistry analysis of acute wounded skin biopsies with a GR-specific antibody targeting phosphorylated (ligand-activated) form of the receptor using the same acute wound skin biopsies used in FIG. 5(A) at 0 hours, 48 hours, and 96 hours post-wounding. Results for the positive control (GC treated skin) and negative control (staining without primary antibody) are also shown.

FIG. 6(A) shows the results of RT-PCR using tissue from non-healing chronic wounds measuring the expression of the enzymes CYP11B, HSD11B1, and HSD11B2. FIG. 6(B) depicts the immunohistochemistry analysis of a chronic wound biopsy stained with a CYP11B-specific antibody. FIG. 6(C) shows the immunohistochemistry analysis of a chronic wound biopsy stained with a GR-phosphorylated-specific antibody.

FIG. 7 shows the results from ELISA assays for cortisol.

FIG. 10(A) shows the histological results of untreated acute wound tissue, acute wound tissue treated with exogenous glucocorticoid, and acute wound tissue treated with metyrapone, an inhibitor of glucocorticoid synthesis. FIG. 10(B) shows the results of immunohistochemistry analysis of acute wound skin biopsies with a GR-specific antibody targeting phosphorylated (ligand-activated) form of the receptor using the same acute wound skin biopsies used in FIG. 10(A).

FIG. 11(A) shows Northern Blot analysis of c-myc expression in untreated and GC treated keratinocytes. FIG. 11(B) shows Northern Blot analysis of c-myc expression in acute wound tissue. FIG. 11(C) shows Western Blot analysis of c-myc protein production in tissue treated with exogenous glucocorticoid and RU486, a glucocorticoid antagonist.

DETAILED DESCRIPTION OF THE INVENTION

Figure 1:
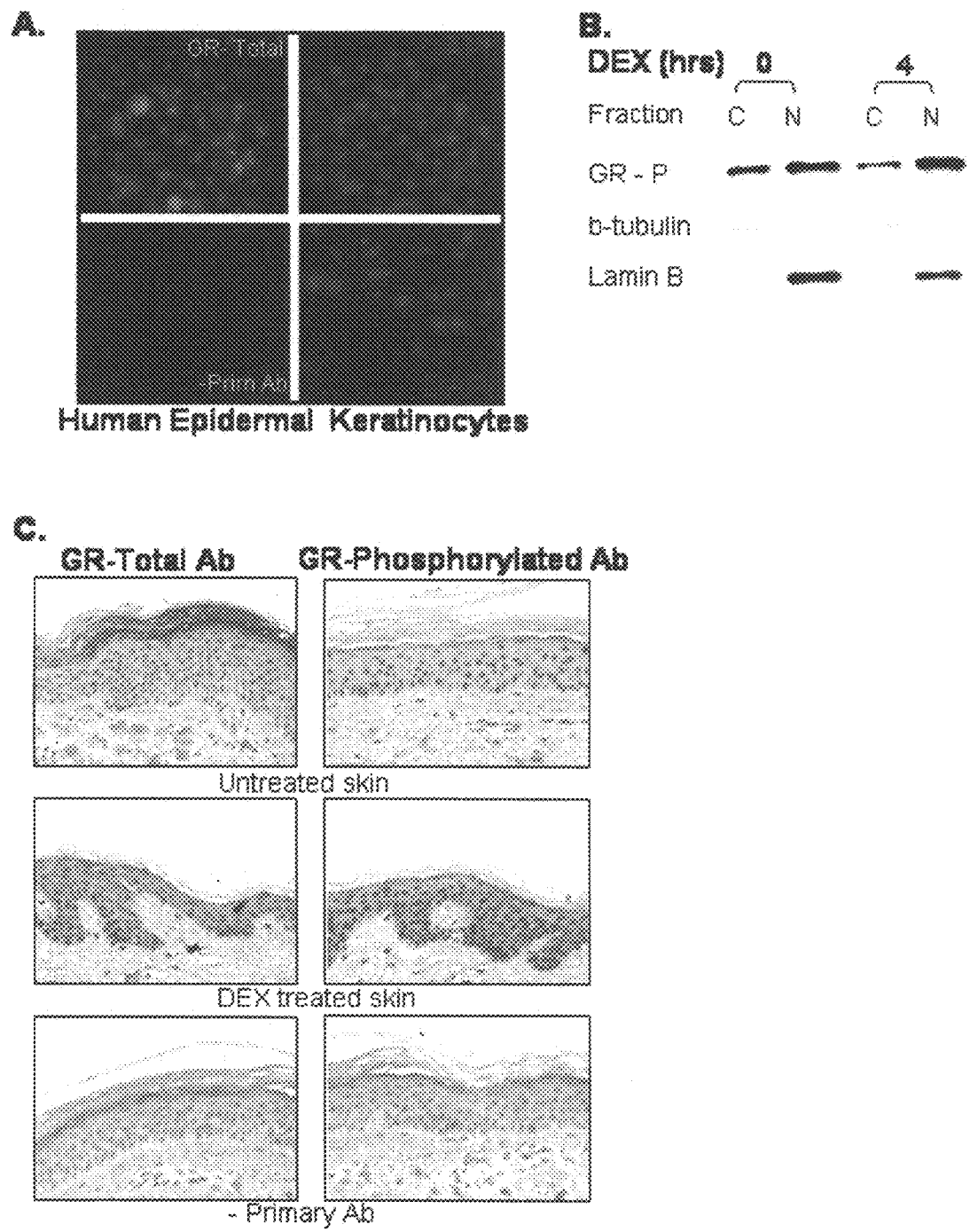
FIG. 1 shows the results proving that the glucocorticoid receptor is hormone activated in epidermis and keratinocytes.

This invention is based in part on the surprising discovery that epidermis is a steroidogenic tissue, meaning it produces and secretes cortisol de novo. Specifically, it has been discovered that epidermal keratinocytes synthesize and secrete cortisol, express CYP11B, an enzyme important for the last step of cortisol synthesis, and show a permanent active glucocorticoid receptor pathway. Upon wounding, cortisol levels increase, which in turn ends the initial pro-inflammatory response, and resets the activated keratinocytes to a normal differentiating state. On the other hand, it has also been discovered that in chronic non-healing wounds which exhibit chronic inflammation, there is misactivated expression of CYP11B and the active GR pathway. These may in synergy contribute to the pathogenesis of chronic wounds. These novel findings have an impact on the understanding, and treatment of anti-inflammatory conditions of the skin, acute wounds, and chronic non-healing wounds.

In order to determine how glucocorticoids (GC) would affect wound healing, the first determination was whether normal epidermis could indeed produce GC. Immunocytochemical analysis was performed using primary keratinocytes grown without a source of GC and a GR-specific antibody. Normal skin biopsies were also stained with both a GR-specific antibody and a GR-specific antibody targeting the hormone-activated, i.e., GC activated, form of the GR. In all three cases, a significant level of glucocorticoid receptor was found in the nuclei, rather than the cytoplasm, indicating GC-activated GR. Because there was no exogenous source of GC, these results indicate activation of the GR by endogenous hormone.

The expression and protein presence of enzymes responsible for GC synthesis and cortisol production in normal healthy skin and keratinocytes was also determined. A considerable level of 11β-hydroxylase (CYP11B) was found in the healthy epidermis. Moreover, CYP11B showed specific tissue distribution in the healthy epidermis. It was predominantly found in the basal and first suprabasal layers of epidermis, which identifies epidermal cell compartments responsible for GC synthesis and indicates a high specificity of expression. Results from RT-PCR and Western blots confirmed the expression of CYP11B in both epidermis and keratinocytes.

It also was found that epidermal keratinocytes and skin tissue produce and secrete cortisol. The amount of cortisol produced and secreted by the skin is surprisingly substantial. ACTH stimulated the production of the cortisol, as did progesterone and IL-1. Metyrapone and IGF-1 inhibit the production of cortisol produced by the skin.

In summary, it was found that the epidermal keratinocytes secrete cortisol, contain the enzyme CYP11B essential for cortisol synthesis and in the intact state, have a constitutive level of GR-pathway nuclear activity. When taken together these data indicate that epidermis is a cortisol producing tissue with constitutive glucocorticoid activity which leads to constitutive activation of the glucocorticoid receptor pathway.

While not being bound to any theory, one reason why the skin produces cortocosteroids is that glucocorticoid may keep the balance of pro-inflammatory cytokines and growth factors. Skin and the epidermis in particular are the first line of defense in protection of the body and thus, have developed mechanisms of alarming the body when there is tissue damage from either mechanical, i.e., wounds, chemical or physical, e.g., UV, sources (Tomic-Canic et al. (1998) *J. Dermatol. Science* 17:167-181). The protective response, which is keratinocyte activation, involves the release of pre-stored IL-1, as well as other pro-inflammatory and growth factors (Freedberg et al. (2001) *J. Invest. Dermatol.* 116:633-640). Thus, it may be possible that the keratinocytes produce corticosteroids to end the activation process and reset themselves back to a normal differentiating state. This hypothesis is further supported by the finding that corticosteroids regulate the expression of epidermal genes utilizing a novel mechanism of four receptor monomers (Jho et al. (2001) *J. Biol. Chem.* 276(49): 45914-45920; Radoja et al. (2000) *Mol. Cell. Biol.* 20:4328-4339) and a specific combination of co-regulators (β-catenin and CARM-1) (Stojadinovic et al. (2005) *Am. J. Pathol.* 167 (1):56-69). It has also been shown that GCs utilize a complex molecular mechanism to block the effects of epidermal growth factor (EGF) (Lee et al. (2005) *J. Mol. Biol.* 345(5): 1083-97)).

Another possible reason as to why the keratinocytes produce corticosteroids is that the avascular epidermis may not have easy access to circulating cortisol, so the tissue needs to make its own supply of the steroid.

It is not believed that the skin serves as an extra-adrenal source of circulating cortisol. Again while not being bound by any theory, it is believed that the skin produces its own cortisol due to the unique properties and features of epidermal tissue. The findings that epidermis produces and secretes cortisol may change the understanding of the biology of epidermis. The current understanding is that inflammatory cytokines exert their action by binding to their respective receptors and triggering signal-transduction cascades that result in transcriptional regulation. In view of these findings regarding the production of cortisol by the epidermis, cytokine signaling has an additional task: to overcome the endogenous basal level of corticosteroid activity in order to reach an effective signaling threshold. In turn, the cytokines may activate additional cortisol synthesis in the skin as it is well established in the immune response to injury, proinflammatory cytokines such as TNF-α, Il-1 and Il-6, act on the hypothalmic, pituitary, or adrenal component of the HPA axis causing an increased release of cortisol. The same mechanism may take place within the epidermis.

Increased $CaCl_2$ levels decrease cortisol production in the skin. $CaCl_2$ is a potent regulator of epidermal differentiation (Morasso and Tomic-Canic (2005) *Biol. Cell* 97(3): 173-83). Thus, differentiation of epidermis may inhibit cortisol production. This is further supported by the distribution of the enzyme CYP11B. The enzyme is found predominantly in the basal and first suprabasal layer of the epidermis. These layers of epidermis are major contributors of tissue repair in that they have the highest proliferative capacity (Li (2004) *J. Clin. Invest.* 113(3):390-400) and are thus, considered as primary targets for pro-inflammatory effects. Corticosteroid synthesis may provide these cells with a balance, i.e., a mechanism of negative feedback.

Both HSD11B1 and HSD11B2 are expressed by epidermis. HSD11B1 would increase glucocorticoid production in epidermis as it is the enzyme responsible for the conversion of cortisone to cortisol. Similarly, HSD11B2 would decrease production of GC in epidermis as it is responsible for the conversion of cortisol to cortisone. The presence of these enzymes in epidermis further shows a mechanism of regulation of cortisol production.

These findings have impact on the treatment of anti-inflammatory disorders with topical corticosteroids. When the enzyme that converts cortisol to inactive cortisone, HSD11B2 is blocked, cortisol levels increase 50% in the skin. This enzyme can impact the efficacy of the exogenous hormone being applied or delivered to the skin. Thus, the treatment of inflammation can also include an inhibitor of HSD11B2, in addition to, or even in place of, the exogenous hormone.

Because epidermis also contains the enzymes CYP11B and HSD11B3, stimulators of these enzymes can also be used in the treatment of inflammation either alone or in combination with an exogenous glucocorticoid. Alternatively, the production of endogenous cortisol can be inhibited by blocking either of these two enzymes. Thus, an inhibitor of CYP11B or HSD11B1 can be delivered or applied to the skin with the exogenous corticosteroid in order to insure only the exogenous steroid is being delivered to the tissue in need of anti-inflammatory treatment.

Other antagonists, e.g., RU486, or agonists, e.g., ACTH, of glucocorticoid production can also be used in methods and compositions to treat inflammation of the skin, either alone or in combination with an exogenous glucocorticoid.

The present invention also has implications as to the treatment of acute and chronic wounds. Normal wound healing begins the pro-inflammatory response of release of cytokines and growth factors. However, keratinocytes need a "stop" signal during acute wound healing responsible for the transition from the activated to normal keratinocyte phenotype.

In acute wounds, induction of the enzyme CYP11B was found, indicating de novo steroidogenesis in this wounded tissue. This induction was found at 48 hours post wounding. Induction of the enzyme HSD11B2 was also found at 48 hours post wounding. Expression of both of these enzymes decreased to basal levels at 96 hours post wounding. The expression of the enzyme HSD11B1, responsible for the conversion of cortisone to cortisol, was found to decrease from 0 hours to 24 hours post wounding and then increased again. These data indicate the de novo synthesis of cortisol during wound healing is tightly controlled by a feed-back mechanism in a temporal manner.

Activation of the glucocorticoid receptor was also found in acute wounds at 48 hours post wounding. This linked pattern shows that the CYP11B enzyme must be present before the GR activation to allow completion of enzyme synthesis, ligand binding, and activation of the GR. Moreover, the activation of the GR pathway takes place at the appropriate time, when the pro-inflammatory signaling needs to be stopped. In other words, the role of glucocorticoids in acute wounds is to act as a wound healing stop signal, re-setting the keratinocytes from wound healing back to a normal, differentiating state. Thus, the production of GCs and activation of the GR in acute wounds appears to follow a model that would promote normal healing of such wounds.

In order to promote or hasten the healing of acute wounds, an agonist and/or stimulator of GC synthesis, such as an agonist or stimulator of CYP11B or other enzyme responsible for GC synthesis could be applied to a subject with an acute wound. Alternatively, an inhibitor of a regulatory enzyme which converts cortisol to cortisone, such as HSD11B2, or a stimulator of an enzyme which converts cortisone to cortisol, such as HSD11B1, could be delivered or applied to a subject with an acute wound. Other agonists of GC production, such as ACTH, could also be used in methods and compositions to treat acute wounds.

In chronic wounds, the model does not follow convention and contributes to the pathological phenotype. Activated GR is needed as the "stop signal" in the acute healing process to neutralize pro-inflammatory cytokines and growth factors, and while the activation of the GR pathway was found in chronic wound tissue, the environment was inflamed. While not being bound by any theory, there are two possible explanations as to why this is the case: either the GR regulatory pathway may be "mis-activated" initially, which in turn causes the overabundance of pro-inflammatory signals as a compensatory mechanism, or pro-inflammatory signals may be initially aberrantly active, thus initiating the GR pathway to neutralize the pro-inflammatory signals. Whichever the cause, this prolonged inflammation is a contributing factor to non-healing wounds. Thus, in chronic wound tissue, prolonged, "misactivated" GR pathway is found.

The expression of the CYP11B enzyme was also found in chronic wound tissue at increased levels in comparison to normal skin, suggesting the continual production of GC in the non-healing edges of the chronic wound. Additionally, the expression of HSD11B2 was at a decreased level in non-healing skin as compared to normal skin.

Moreover, the CYP11B distribution pattern in chronic wound tissue is atypical of the pattern in healthy skin and acute wounds. The enzyme is not found in the basal layer but only in the supra basal layer of chronic wound identifying an atypical and misactivation of cells in the chronic wounds.

Taken together, these results suggest increased production of cortisol in chronic wounds by two different mechanisms: one by increasing synthesis of cortisol and one by blocking conversion of cortisol to inactive cortisone. The increased expression of CYP11B coupled with decreased levels of HSD11B2 and the atypical distribution of CYP11B in the non-healing edge of chronic wounds indicates that the aberrant synthesis of glucocorticoids in chronic wounds and loss of regulation by HSD11B2 contributes to the pathogenesis of chronic ulcers.

Thus, in order to promote or hasten the healing of chronic non-healing wounds, an antagonist and/or inhibitor of GC synthesis, such as RU486, or an antagonist and/or inhibitor of CYP11B or other enzyme responsible for GC synthesis, could be administered or applied to a subject with a chronic non-healing wound. Additionally, an agonist or stimulator of the enzyme HSD11B2 or the like would also decrease the GC production in the chronic non-healing tissue.

The atypical pattern of CYP11B distribution in chronic wound tissue can be used to determine if the tissue is producing GC aberrantly and in need of treatment. Such a method would involve obtaining a biopsy or sample from the chronic wound, preferably from the non-healing edge and determining the location of the enzyme in the epidermis layers. Any method known in the art for such localization can be used. The preferred method is staining the skin sample with an antibody to total CYP11B. This method requires preparing the skin and incubating it with the antibody, then adding a biotinylated secondary antibody for visualization. If the CYP11B is localized in the supra-basal layer of the epidermis and not the basal layer, this indicates that the tissue is producing GC aberrantly and treatment with a GC antagonist/inhibitor is indicated.

The gene expression profile of the chronic non-healing wound can be used to determine if the chronic non-healing wound is producing GC aberrantly and in need of treatment. To perform this method, one or more tissue samples or biopsies are taken from within or adjacent to a chronic wound, preferably at the non-healing edge of the wound. A gene expression profile is then determined for the cells in the site or sites of the tissue biopsies. This gene expression profile is compared to a known gene expression profile from healthy skin. Specifically, if the chronic non-healing tissue expresses the enzyme CYP11B at an increased level and the enzyme HSD11B2 at a decreased level, this indicates that the chronic non-healing tissue is producing GC aberrantly and should be treated with a GC antagonist of the present invention.

Expression of CYP11B and HSD11B2 proteins in tissue from chronic wounds can also be compared to that in normal skin. Again if the expression of CYP11B is increased in the chronic wound tissue as compared to the normal skin, and the expression of HSD11B decreased, the chronic non-healing wound tissue is producing GC aberrantly and should be treated with a GC antagonist/inhibitor of the present invention.

Any method known in the art can be used to determine the expression profile of tissue from non-healing tissue and healthy tissue. These methods include RT-PCR and microarray technology.

It has been previously determined that activated glucocorticoid receptor can dominantly block the effects of epidermal growth factor (EGF) during wound healing (Lee et al. (2005) *J. Mol. Biol.* 345:1083-1097). It has also been previously shown that EGF may contribute to growth of cancer cells, including those which are epithelial derived (Johnston et al. (2006) *Curr. Med. Chem.* 13(29):3483-92). Thus, agonists and/or stimulators of the corticosteroid synthesis pathway, which in turn activates the glucocorticoid receptor pathway, can be applied to the skin to inhibit the development and growth of epithelial-derived cancer cells by blocking EGF-mediated cellular migration and invasion in a subject in need of such treatment.

It has been previously shown that glucocorticoids can be used to treat keloids, fibrotic or hypertrophic scars (Rosen et al. (2007) *Plast. Reconstr. Surg.* 120:1395-4000; Jalali et al. (2007) *Surgeon* 5:175-80; Wu et al. (2006) *J. Invest. Dermatol.* 126:1264-1271; Tang et al. (1992) *Brit. J. Plastic Surg.* 45:371-373). Thus, agonists and/or stimulators of the corticosteroid synthesis pathway can be applied to the scar for any treatment purpose, including, but not limited to, inducing regression of the scar and prevention of recurrence of the scar in a subject in need of such treatment Known antagonists of corticosteroids include RU 486 which is the commonly known name of mifepristone. Mifepristone is a synthetic steroid composition with the chemical name 11β-[p-(dimethylamino)phenyl]-17β-hydroxy-17-(1-propynyl)estra-4,9,dien-3-one. It is also an inhibitor of progesterone. Other known antagonists of corticosteroids would include $CaCl_2$ and metyrapone, which blocks cortisol synthesis. Additionally, inhibitors of any enzyme that is responsible for the synthesis of GC or the conversion of inactive cortisone to active cortisol, could be used as antagonists in the present invention. A stimulator of any enzyme that is responsible for the conversion of cortisol to cortisone would also be an antagonist for use in the present invention.

Known agonists of corticosteroids include adrenocorticotropic hormone (ACTH) (stimulates synthesis of glucocorticoid), CBX (regulates metabolism of glucoocortocoid), and any other of a number of compounds including synthetic corticosteroids, such as dexamethasone, betamethasone valerate, and clobetasole propionate. Additionally, stimulators of any enzyme that is responsible for the synthesis of GC or the conversion of inactive cortisone to active cortisol, could be used as agonists in the present invention. An inhibitor of any enzyme that is responsible for the conversion of cortisol to cortisone would also be an agonist for use in the present invention.

The preferred embodiment of the methods and compositions of the present invention is topical administration, wherein the composition is applied directly to the skin. However, in some cases, intradermal injection, i.e., injection of the composition just under the skin, may be desirable. An example of such a case would be if a high concentration of composition is needed at the affected area.

For topical administration to the epidermis the compounds of the invention are mixed with or suspended in an inert carrier. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E.W. Martin.

The topical compositions of the present invention may be formulated as creams, gels, ointments, or lotions. Such compositions may, for example, be formulated with an aqueous or oily base with the addition of suitable thickening, gelling, emulsifying, stabilizing, dispersing, suspending, and/or coloring agents.

Creams are the most commonly used topical preparation and are emulsions of oil in water. They are easy to apply and appear to vanish when rubbed into the skin.

Gels are water based substances thickened without oil or fat. Gels are not absorbed as well by the skin as preparations containing oil or fat.

Ointments contain a lot of thick oil and very little water. While ointments feel greasy, they are the best vehicle for delivering active ingredients to the skin.

Lotions are similar to creams but contain more water. They are suspensions of finely dispersed powdered material in a base of water or oil and water. Lotions are easy to apply and are particularly useful for cooling and drying the skin.

In addition to antagonists or agonists of the present invention, the topical composition may additionally include a corticosteroid such as alclometasone, amcinonide, betamethasone, clocortolone, desonide, desoximetasone, diflorasone, flucinolone, flucinonide, flurandrenolide, fluticasone, halcinonide, halobetasol, hydrocortisone, mometasone, and triamcinolone. The compositions may also include additional agents, such as protective agents, and symptom-relieving agents, i.e., agents that relieve itching and pain.

Inflammation of the skin can have many causes. One of the most common causes is contact dermatitis which is an inflammation caused by contact with a particular substance, such as poison ivy or other plants, cosmetics, drug in skin creams such as antibiotics, and chemical used in clothing. The methods and compositions of the present invention could be used to treat skin inflammation caused by contact dermatitis. Atopic dermatitis caused by allergies also causes skin inflammation and can be treated using the methods and compositions of the present invention.

The terms used in this specification generally have their ordinary meanings in the art, within the context of the invention, and in the specific context where each term is used. Certain terms are discussed below, or elsewhere in the specification, to provide additional guidance to the practitioner in describing the compounds, compositions, and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

The terms "prevent" or "prevention", as used herein, refer to the partial or complete inhibition of the development of a condition that impairs the performance of a function of the human body.

The terms "treat" or "treatment", as used herein, refer to an attempt to ameliorate a disease condition or to relieve or alleviate at least one symptom associated with such condition, or to slow or reverse the progression of such condition.

Still further, the terms "effective amount" and "therapeutically effective amount" refer to that amount of the compound or composition determined by the skilled artisan to effectively prevent, suppress or treat the targeted condition. The effective amount of a compound or composition will be determined empirically by administering a range of dosages to the patient and observing that dosage which is most effective for the treatment of the condition and best tolerated by the patient. The method of making such a determination will be readily understood by the skilled artisan and will necessarily take into account such factors as, inter alia, the route of administration, formulation, and the condition, age, sex, height, and weight of the patient.

The terms "agonist" and "stimulator" refers to an agent, compound, composition, or drug that promotes, enhances, stimulates, or potentiates a physiological or enzymatic action or increased functional activity.

The terms "antagonist" or "inhibitor" means an agent, compound, composition, or drug that blocks, restrains, reduces, or retards a physiological or enzymatic action or functional activity.

The term "subject" as used in this application means an animal with an immune system such as avians and mammals. Mammals include canines, felines, rodents, bovine, equines, porcines, ovines, and primates. Avians include fowls, songbirds, and raptors. The invention is therefore useful in dogs, cats, mice, rats, rabbits, cows, horses, pigs, sheep, goats, apes, monkeys, chickens, turkeys, canaries, eagles, hawks, owls, and, particularly humans. Thus, the invention can be used in veterinary medicine, e.g., to treat companion animals, farm animals, laboratory animals in zoological parks, and animals in the wild. The invention is particularly desirable for human medicine applications.

The terms "array" or "microarray" are used interchangeably and refer generally to any ordered arrangement (e.g., on a surface or substrate) of different molecules, referred to herein as "probes." Each different probe of any array is capable of specifically recognizing and/or binding to a particular molecule, which is referred to herein as its "target" in the context of arrays. Examples of typical target molecules that can be detected using microarrays include mRNA transcripts, cRNA molecules, and proteins.

The following Examples demonstrate various embodiments of the claimed invention. However, they should not be construed as limiting its scope.

EXAMPLES

Example 1

Materials and Methods

A. Human Specimens and Wounding
Acute Wounds
Human skin specimens were obtained from discarded tissue in reduction mammoplasty following approved Hospital for Special Surgery protocol (#25121). Preparation of tissue with acute wounds was done as previously described (Tomic-Canic et al. (2007) *Wound Repair Regen.* 15(1):71-9); Stojadinovic et al. (2005) *Am. J. Pathol.* 167(1):59-69). The adipose tissue was removed, and circular templates of skin were generated using a 6 mm biopsy punch. A 3 mm biopsy punch was used to create an acute wound. The skin specimens were maintained at the air-liquid interface with DMEM (BioWhittaker, Walkersville, Md.) with antibiotics-antimycotics, and fetal bovine serum (FBS) (Gemini Bio-Products, Woodland, Calif.) for 0, 4, 48, and 96 hours in the presence or absence of 1 μM dexamethasone (Sigma, St. Louis, Mo.). Acute wounds were fixed in 4% paraformaldehyde (Sigma) at room temperature overnight, dehydrated with ethanol, cleared in chloroform, and embedded in paraffin.

Chronic Wounds

Chronic wound tissue was obtained from discarded tissue of biopsies of consenting patients having surgical debridement using approved Columbia University protocol.

B. Immunohistochemistry

Six μm tissue sections were serially cut on a microtome (HM 315, Carl Zeiss, New York, N.Y.) and mounted on slides. Sections were dewaxed in xylene, re-hydrated and washed with 1× phosphate buffered saline (PBS). For antigen retrieval, paraffin sections were heated in a 95° C. water bath in Target Retrieval Solution (DAKO Corporation, Carpinteria, Calif.). Histological slides were treated with 3% $H_2O_2$/30% MeOH for 30 minutes, rinsed with water, and blocked with normal rabbit serum for 30 minutes (Vectastatin Kit Elite ABC, Vectorlabs, Burlingame, Calif.). Sections were then incubated with total CYP11B antibody (1:500) (Chabre et al. (2000) *J. Clin. Endo. and Metabol.* 85:4060-4068), GR total antibody (1:100) (Affinity Bioreagents, Golden, Colo.), and GR total antibody (1:1000) (gift from Dr. Ines Rogatsky, Hospital for Special Surgery), or anti-phospho-Ser211 antibody (1:250) (obtained from Dr. Michael Garabedian, New York University School of Medicine, as described in Ismaili et al. (2004) *Annals of NY Acad. Science* 1024:86-101, and Wang and Garanedian (2003) *J. Biol. Chem.* 278(51):50897-901), in a commercially available antibody diluent (DAKO Antibody Diluent with Background Reducing Components, DAKO Corporation) for one hour at room temperature. A rabbit biotinylated secondary antibody was added and avidin-biotin complex was visualized using DAB (DAB Peroxidase Substrate Kit, Vectorlabs). Slides were counterstained with hematoxylin. For negative controls, 1×PBS was substituted for primary antibody. Sections were analyzed using a Carl Zeiss microscope. Digital images were taken with Adobe TWAIN_32 program.

C. Cell Culture

Normal human epidermal keratinocytes were initiated using 3T3 feeder layers as previously described (Randolph and Simon (1993) *J. Biol. Chem.* 268(13):9198-9205) and frozen in liquid nitrogen until use. Once thawed, the keratinocytes were grown without feeder cells in defined serum-free keratinocyte medium supplemented with epidermal growth factor and bovine pituitary extract (keratinocyte-SFM, GIBCO, Carlsbad, Calif.). Cells were expanded through two 1:4 passages before they were grown to 80% confluency. Cells were washed several times with 1×PBS before they were incubated with basal keratinocyte medium (GIBCO) custom made without hydrocortisone and thyroid hormone.

D. Cellular Fractionation and Western Blot

Keratinocytes were grown to 80% confluency, switched to the basal media for 24 hours, and incubated with 1 mM dexamethasone (Sigma) for 24 and 48 hours. Cells were harvested by trypsinization and cytoplasmic and nuclear fractions were obtained using Nuclear Extract Kit (Active Motif, Carlsbad, Calif.) following commercial protocol. 15 µg of each fraction was separated on a 10% SDS-PAGE gel. The proteins were then transferred to a nitrocellulose membrane (Protran®, Bioscience, Dassel, Germany) using the semi-dry transfer system (BioRad, Hercules, Calif.). Ponceau S was used to check the efficiency of the transfer. The membrane was subsequently blocked by 3% BSA for 2 hours at room temperature. The membrane was washed 3 times for 5 minutes in TTBS and then incubated at 4° C. overnight with GR antibody (1:500) (Affinity Bioreagents) followed with horseradish protein (HRP) conjugated to anti-rabbit secondary antibody (1:1000) (Santa Cruz Biotech, Santa Cruz, Calif.). Immune complexes were visualized using Super Signal West Pico Chemiluminescent substrate (Pierce, Rockford, Ill.). Immunoblot was exposed on x-ray film (HyBlot CL, Denville, N.J.) according to manufacturer's instruction.

Subsequently the membrane was stripped (3 times for 5 minutes in TTBS) and re-probed overnight at 4° C. with b-tubulin (1:1000) (Santa Cruz Biotech) used as a loading control for cytoplasmic proteins and Lamin B3 (1:1000) (Santa Cruz Biotech) used as a control for nuclear proteins.

E. ELISA Assay for Cortisol

Cells were cultured to 80% of confluency as described above in Example 1(C). 200 µl of the medium was collected at 0, 6, 12, 24, and 48 hours after the switch to basal medium, and cortisol production was measured using ELISA kit (R & D Systems, Minneapolis, Minn.) following commercial protocol.

F. Immunocytochemistry

Human epidermal keratinocytes were grown to 40% confluence in serum free keratinocyte low Ca medium. The cells were incubated for 24 hours in basal serum-free medium and treated with or left without 1 µM dexamethasone (Sigma) for 24 hours. Cells were stained using total GR antibody (1:250) (Affinity Bioreagents) following previously published protocol (Stojadinovic et al. (2005) *Am. J. Pathol.* 167(1):59-69).

G. Real Time Polymerase Chain Reaction (RT-PCR)

RNA isolation and purification was performed using Triazol (Invitrogen, Carlsbad, Calif.) extraction and subsequent Qiagen RNeasy Kit column purification (Qiagen, Alameda, Calif.). Reverse transcription and amplification were performed using primers CYP11B1 fw GCTAGACATAGGGGCTCC (SEQ ID no. 1), CYP11B1-rev AGGTGTTTCAGCACATGG (SEQ ID no. 2)and Access RT-PCR Kit (Promega, Madison, Wis.) as follows: (a) reverse transcription—1 cycle at 48° C. for 45 minutes; (b) AMV RT inactivation and RNA/cDNA primer denaturation—1 cycle at 94° C. for 2 minutes; (c) second strand cDNA synthesis and PCR amplification—35 cycles: denaturation for 30 seconds, annealing at 51° C. for 1 minute and extension at 68° C. for 2 minutes; and (d) final extension—1 cycle at 68° C. for 7 minutes. Samples were separated by electrophoresis on 2% agarose gels containing 0.5 µg/ml of ethidium bromide and visualized under UV light.

Example 2

Hormone Activated Glucocorticoid Receptor (GR) is Present in Untreated Human Epidermis and Primary Keratinocytes Primary human keratinocytes were grown in culture as described above in Example 1(C) and localization of the GR was established using a GR-specific antibody and a fluorescent dye used to stain nuclei, 4'-6-diamidino-2-phenylindole (DAPI) (Sigma), as described in Example 1(F). The results, as shown in FIG. 1(A), established that the GR localized predominantly to the cell nuclei suggesting significant activation of the GR.

To further evaluate the GR activity, Western Blot as described in Example 1(D), was used to analyze cytoplasmic and nuclear protein fractions for the presence of hormone activated receptor, GR-P (Wang and Garabedian (2003) *J. Biol. Chem.* 278:50897-901). As shown in FIG. 1(B), there was a significant presence of GR-P (activated GR) in the nuclear fraction of the keratinocytes, confirming the activation of the GC pathway in keratinocytes grown in cortisone-free medium.

To further test the activation of GR in epidermis, five different specimens of normal human skin were stained with both GR-specific antibodies as described in Example 1(B). As shown in FIG. 1(C) (data from one sample), GR localized to the nucleus of approximately half of the cells in the epidermis suggesting activation of the glucocorticoid receptor.

To confirm the hormone activation of the glucocorticoid receptor, sections of the same specimens were stained with GR-specific antibody targeting phosphorylated, hormone-activated form of the GR as described in Example 1(B). A similar pattern to the staining with the GR-specific antibody was found. As shown in FIG. 1(C), phosphorylated, hormone-activated GR was found in half of the cells in epidermis of human skin. As expected, topical glucocorticoid treatment of the skin for 24 hours further activated the receptor, as additional GR localized predominantly in the nucleus (FIG. 1(C)). These data support the hypothesis that there is substantial activation of the GC pathway in epidermal keratinocytes.

Example 3

CYBP11 is Expressed in the Epidermis and Keratinocytes

Multiple approaches were used to determine if CYBP11, an enzyme responsible for final glucocorticoid synthesis (converting 11-deoxycortisol to cortisol), is present and expressed in the epidermis.

Using biopsies of normal human skin and a CYP11B specific antibody, immunohistochemistry as described in Example 1(B), was performed to determine protein presence and localization. The results showed that the CYP11B is present in epidermis. Surprisingly, CYP11B is very specifically distributed in the epidermal tissue. The enzyme is predominantly present in basal and first suprabasal keratinocytes, suggesting a high specificity of expression (FIG. 2A).

Figure 2:
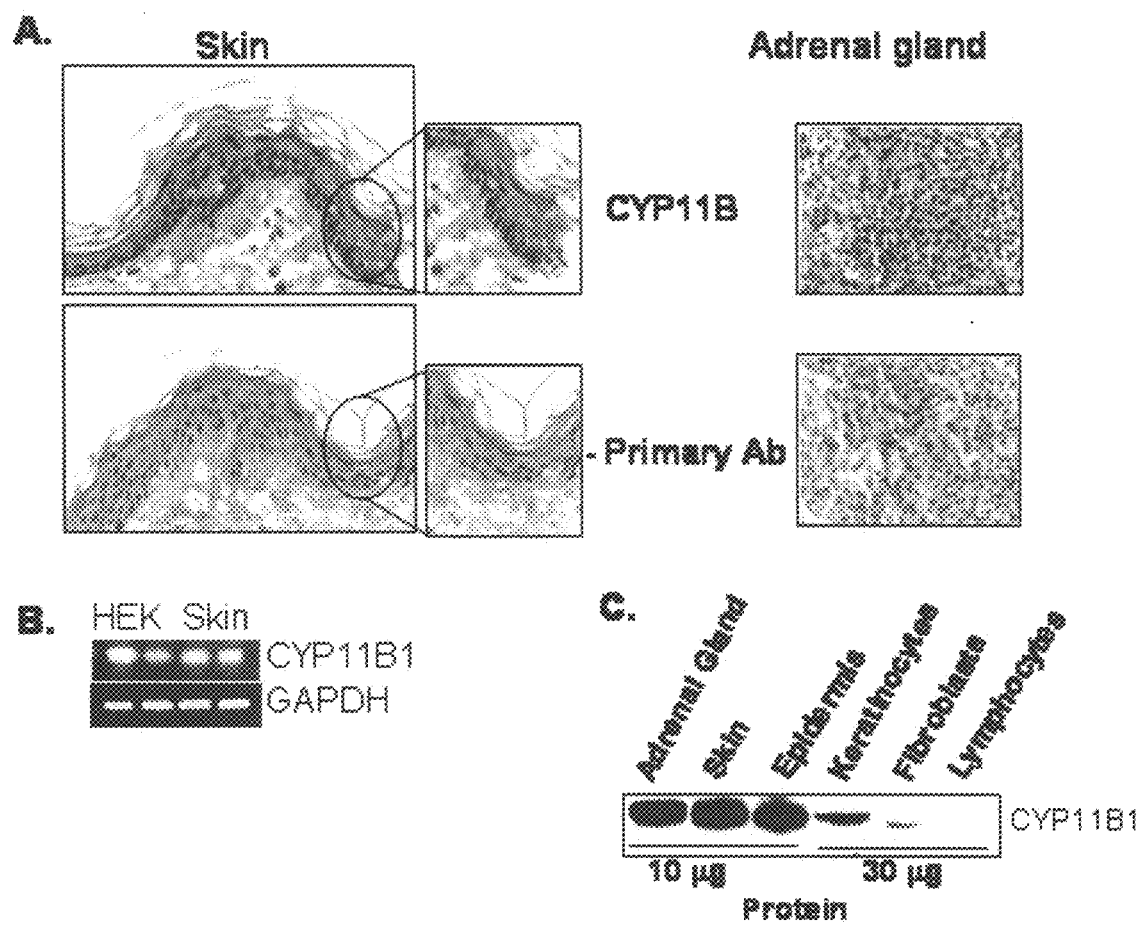
FIG. 2 depicts the results showing that CYP11B is expressed in the epidermis.

It was confirmed that CYP11B is expressed in both primary keratinocytes and skin biopsies using RT-PCR as described in Example 1(G) (FIG. 2B).

Finally, proteins were extracted from skin biopsies, epidermis, keratinocytes, and dermal fibroblasts, and analyzed using anti-CYP11B antibody described in Example 1(B) and Western Blots as described in Example 1(D). As shown in FIG. 2(C), the presence of CYP11B protein was found in each sample. The amount of CYP11B protein in skin and epidermis was surprisingly excessive, but this data was not completely quantitative since mouse adrenal gland was used as a positive control. Cultured keratinocytes expressed much more CYP11B than fibroblasts, but the amount of the enzyme detected in the cells was much smaller than in skin and epidermis. The obtained signal was specific and was not detected in the negative control, lymphocytes which do not express CYP11B (Zhou et al. (1998) *Mol. Cell Endocrin.* 138:61). These results also confirmed that CYP11B protein is present in human skin (FIG. 2C).

Example 4

Primary Keratinocytes and Skin Produce and Secrete Cortisol

Figure 11:
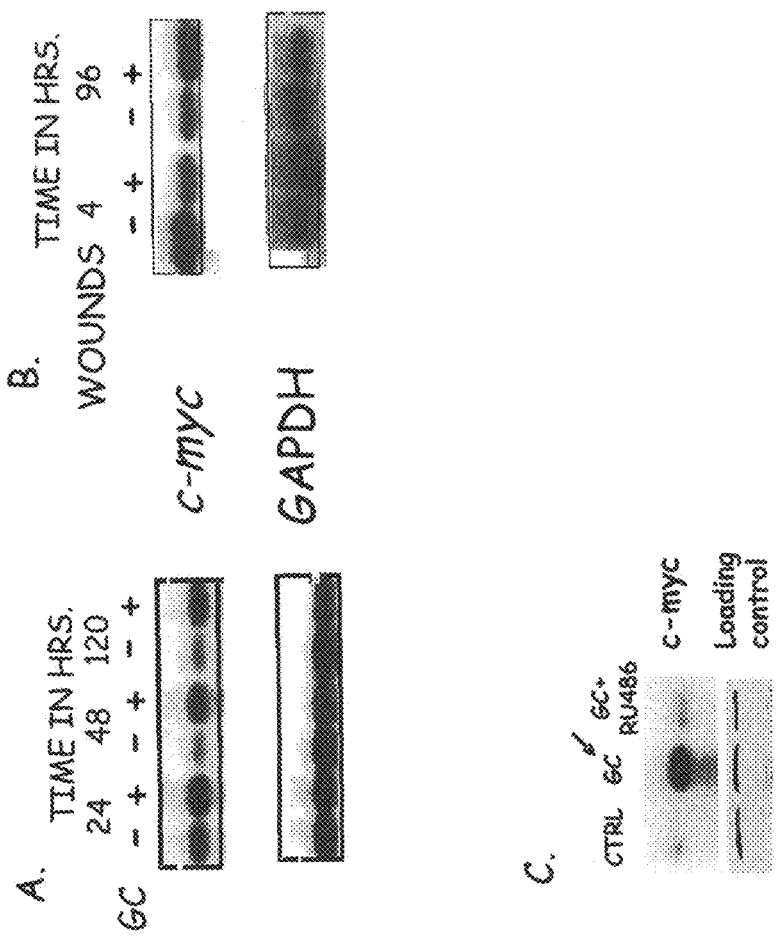
FIG. 11 depicts Northern Blot and Western Blot analyses measuring c-myc expression and protein production in keratinocytes and acute wound tissue.

To further confirm that keratinocytes produce glucocorticoids de novo, medium was collected from cultured cells grown in the minimal medium in the absence of any alternative GC source as described in Example 1(C). Cortisol production was measured after 0, 6, 12, 24, and 48 hours using the ELISA assay described in Example 1(E). The level of cortisol in the medium was 0.163 ng/ml as shown in FIG. 3(A). To confirm the production in tissue, the production of cortisol released from skin in explant cultures was measured. As shown in FIG. 3(B), 11.1 ng/ml of cortisol was released by the skin.

To confirm that the production occurs in the keratinocytes and tissue, 0.1mM of ACTH was added. Cortisol levels in both keratinocytes in culture and skin explants were induced 2.7 and 2.01 fold, respectively (FIG. 3). This statistically significant increase in ACTH treated cells and tissues confirms cortisol production in situ.

Example 5

Cortisol Production and Regulation During Acute Wound Healing

Figure 4:
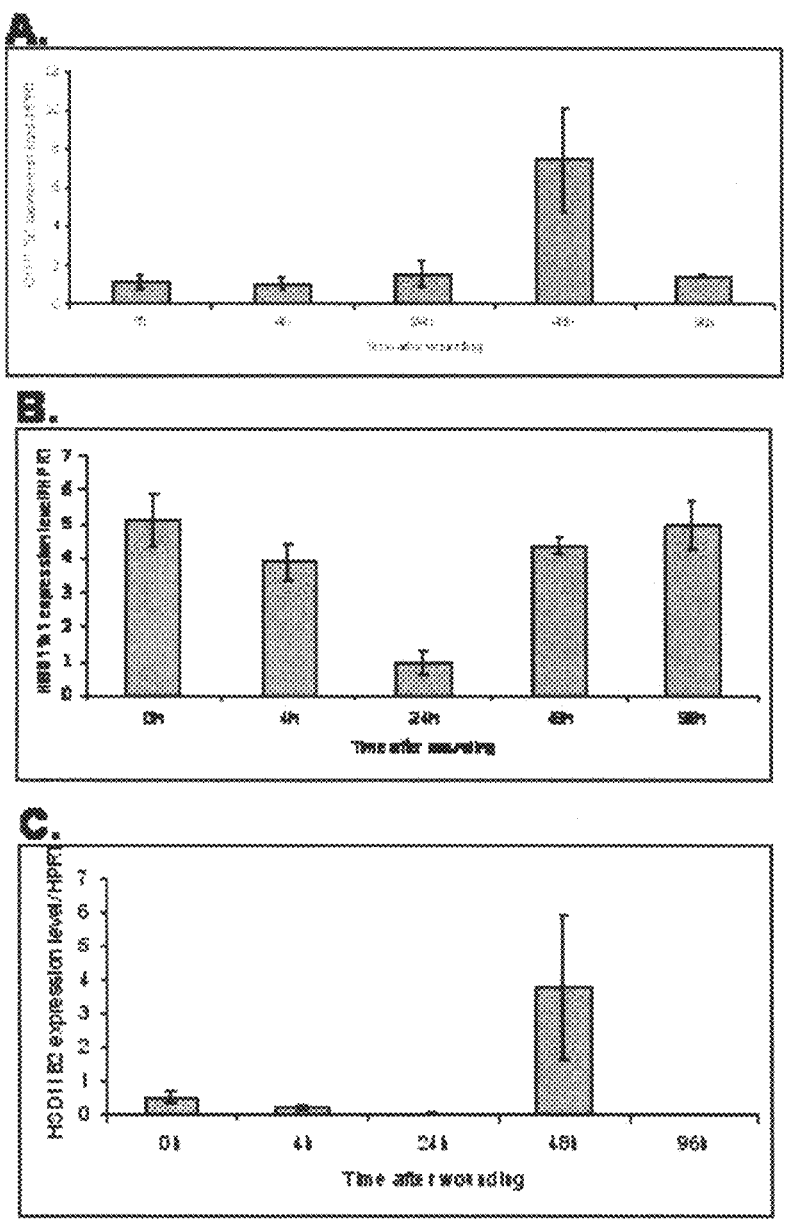
FIGS. 4(A), 4(B) and (C) shows the results of RT-PCR using acute wound tissue at 0, 4, 24, 48, and 96 hours post wounding, and primers specific for CYP11B (FIG. 4(A)), HSD11B1 (FIG. 4(B)), and HSD11B2 (Figure (C)).
FIG. 4(D) shows the immunohistochemistry analysis of acute wounded skin biopsies stained with anti-CYP11B antibody at 0 hours, 48 hours, and 96 hours post-wounding. Results for the positive control (adrenal gland) and negative control (staining without primary antibody) are also shown.

Glucocorticoid activation in acute wound healing was tested using the acute wounding model described in Example 1(A). Acute wounds were maintained at 0, 4, 48, and 96 hours post-wounding at the air-liquid interface. RT-PCR as described in Example 1(G) was performed using primers specific for the enzymes CYP11B (responsible for last step of cortisol synthesis), HSD11B1 (responsible for conversion of inactive cortisone to active cortisol), and HSD11B2 (responsible for conversion of active cortisol to inactive cortisone) (FIGS. 4 (A), (B), and (C)). As shown in FIG. 4(A), expression of CYP11B was 6.5 fold induced 48 hours after wounding. At the same time, a 4 fold induction of HSD11B2 was found (FIG. 4(C)). Moreover, the expression of both CYP11B and HSD11B2 were decreased to basal levels at 96 hours post wounding (FIGS. 4(A) and 4(C)). The expression of HSD11B1 was decreased 3.6 fold 24 hours after wounding and gradually increased after 24 hours post wounding and reached base levels at 48 hours post wounding (FIG. 4(B)). The expression of HSD11B1 was also higher than expression levels of HSD11B2 and CYP11B1 during all time points including unwounded skin.

Figure 4D:
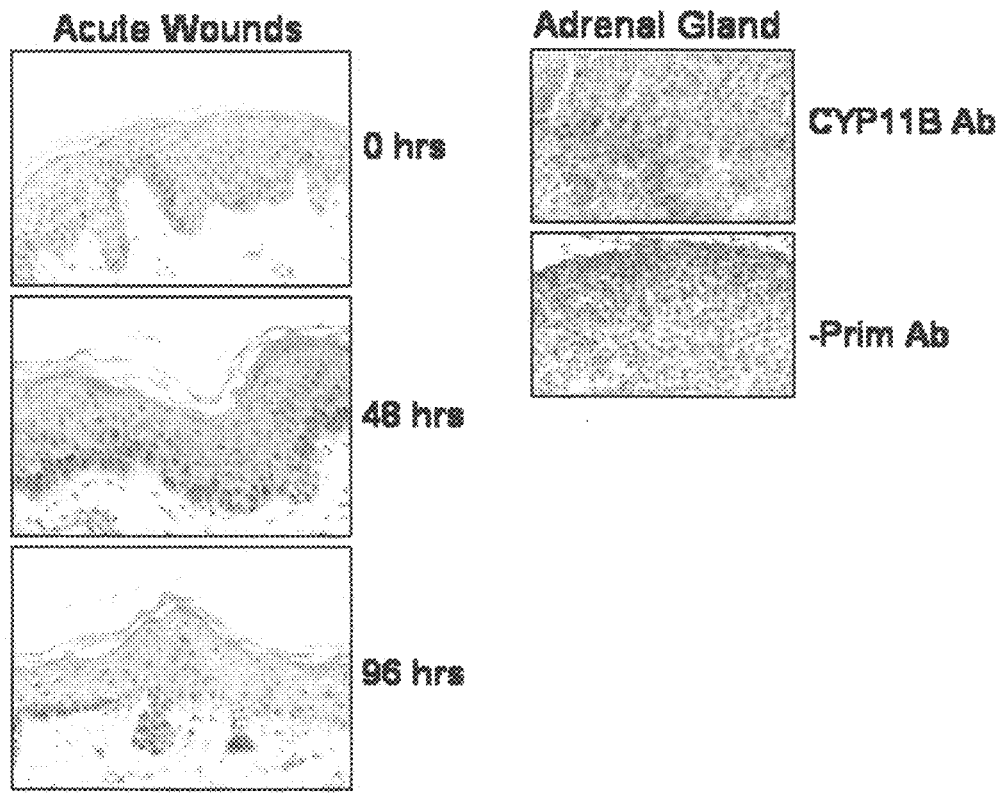

To confirm the data from RT-PCR, sections of acute wounds were stained with anti-CYP11B antibody as described in Example 1(B). As shown in FIG. 4(D), strong staining was found in the sections from wounds 48 hours post wounding. Staining was most prominent in the basal layer of the epidermis, suggesting basal cells may be the dominant source of synthesis. This data confirmed that CYP11B is induced at both the mRNA and protein level at 48 hours post wounding.

Sections of the acute wounds were also stained with the GR-specific antibodies as described in Example 1(B). As shown in FIG. 5(A), no significant staining was seen at 0 hours. Both cytoplasmic and nuclear staining was found 48 hours post-wounding. A significant portion of GR remained in the nucleus through 96 hours post wounding (FIG. 5(A)), which is in correlation with the expression profiles of CYP11B, HSD11B1, and HSD11B2. The positive control, GC treated skin, showed a similar pattern thus confirming activation of the GR pathway during acute wound healing (FIG. 5(A)).

To confirm the activation of the GR, the GR-P-specific antibody described in Example 1(B) was used to stain the same acute wound sections. As shown by FIG. 5(B), a similar staining pattern to total GR antibody was found. There was no staining at 0 hours (FIG. 5(B)). Analogous to the results with the total GR antibody staining, cytoplasmic and nuclear staining was apparent at 48 hours and that staining was maintained 96 hours post-wounding (FIG. 5(B)). The positive control, GC treated skin, showed similar results to 48 hour acute wounded skin (FIG. 5(B)).

From these data, it is concluded that GC synthesis and regulation, as well as GR activation occurs during the acute process of wound healing in a timed response manner.

Example 6

Cortisol Production and Deregulation in Chronic Wounds

The activation and regulation of cortisol synthesis and metabolism in acute wound healing raised the question of cortisol production in chronic non-healing wounds.

RT-PCR was performed using samples obtained from the biopsies of patients with non-healing wounds as described in Example 1(A) and the primers for CYP11B, HSD11B1, and HSD11B2 describes in Example 5 was performed. Expression of these enzymes in the biopsies from the wounded skin was compared to the expression of these enzymes in normal skin. Surprisingly, the expression of CYP11B1 in chronic wounds was increased 2.9 fold in comparison to normal skin, whereas the expression of HSD11B2 was 2.3 times decreased as compared to normal skin (FIG. 6(A)).

To confirm these results, CYP11B-specific antibody was used to stain tissue from the non-healing edge of patients with chronic wounds. As shown in FIG. 6(B), there is strong expression of CYP11B in the epidermis of the non-healing edge of the chronic wounds. An atypical pattern of CYP11B staining was observed that excluded expression of the CYP11B in the basal layer of the keratinocytes. CYP11B was detected in the sub-basal layer in contrast normal skin and acute wounds.

To confirm that the increase in CYP11B activates the GR pathway in chronic wound tissue, biopsies obtained from the non-healing edges of patients with chronic ulcers were also stained with the GR-P-specific antibodies as described in Example 5. The GC-treated skin (positive control) exhibited nuclear and cytoplasmic staining demonstrating activation of the GR. Strong nuclear and cytoplasmic staining of the hyperproliferative epidermis of the chronic wounds as shown in FIG. 6(C) indicates GR activation in non-healing, chronic wounds.

Example 7

Figure 7A:
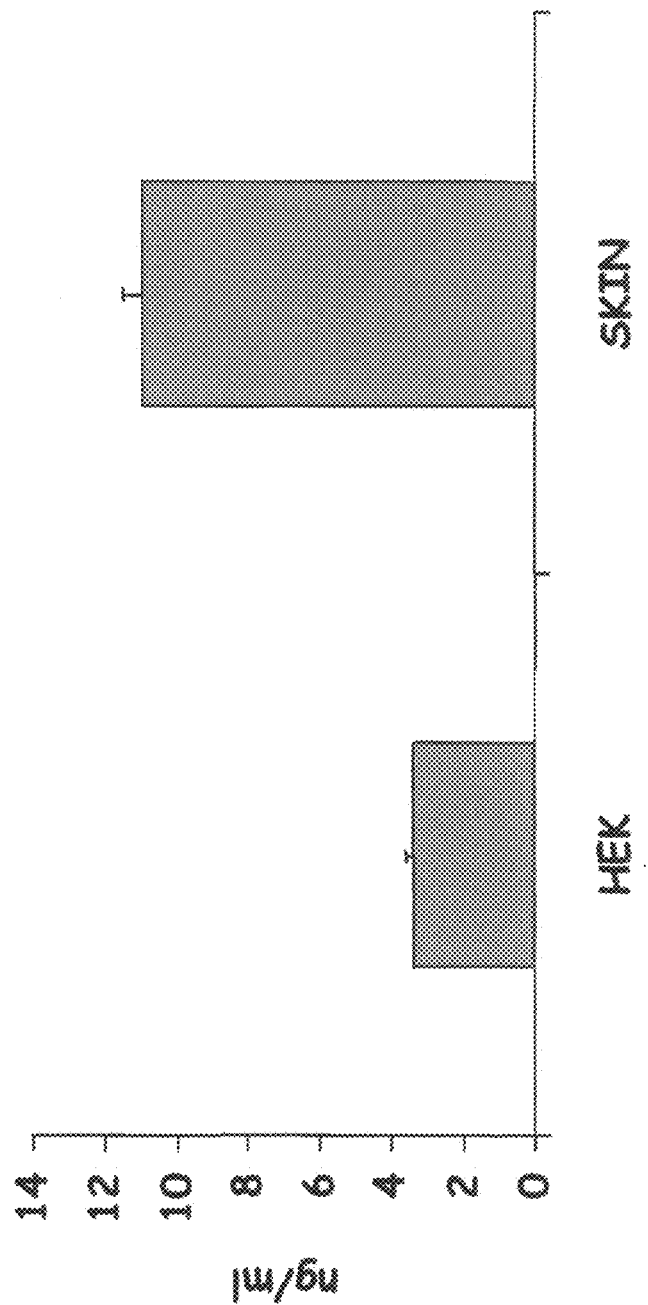
FIG. 7(A) shows the results of ELISA assays performed on collected medium from primary human keratinocytes grown in minimal media with no alternative source of glucocorticoid and from skin explant cultures.

De Novo Cortisol Synthesis in Keratinocytes and Skin can be Stimulated by ACTH and Progesterone and Inhibited by Metyrapone To further confirm that keratinocytes produce glucocorticoids de novo, medium was collected from cultured cells grown in the minimal medium in the absence of any alternative GC source as described in Example 1(C). The production of cortisol released from skin explant cultures was also measured. The amount of cortisol production was measured using the ELISA assay described in Example 1(E). As shown in FIG. 7(A), the level of cortisol found in the medium from the keratinocytes was 3.38 ng/ml.

Figure 7B:
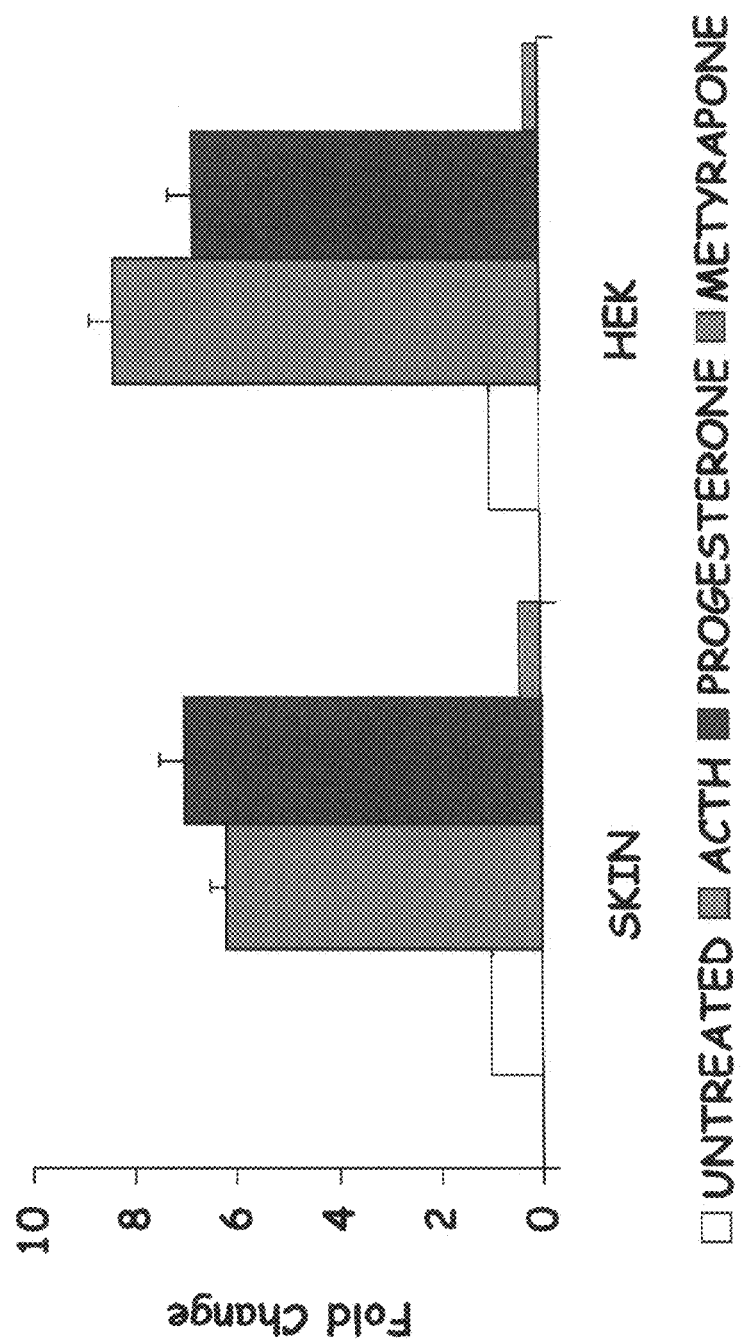
FIG. 7(B) depicts the fold change of cortisol synthesis between untreated skin and keratinocytes, and those treated with ACTH, progesterone, and metyrapone.

A further experiment was performed where prior to measurement both the keratinocytes and the skin explant cultures were stimulated with 0.1 µM of ACTH. Cortisol production was measured after 24 hours using the ELISA assay described in Example 1(E). The induction of cortisol levels in both the keratinocytes and skin explants were statistically increased ($p<0.01$) in ACTH treated cells and tissues, by 2.7 and 2.0 fold, respectively (FIG. 7B). The addition of 1 µM of progesterone as a substrate for glucocorticoid synthesis lead to a 2.5 fold induction in cortisol production in both cells and skin (FIG. 7B). The addition of 200 µM metyrapone (Sigma) decreased endogenous levels of cortisol production (FIG. 7B).

Example 8

Figure 8:
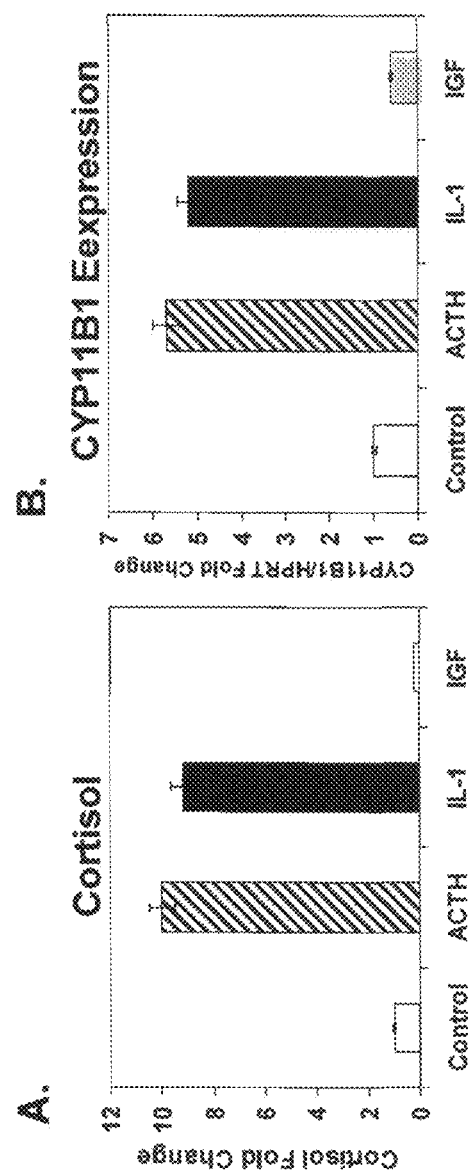
FIG. 8(A) shows the results from ELISA assays for cortisol. Assays were performed on collected medium from primary keratinocytes grown in minimal media with no alternative source of glucocorticoid and from skin explant cultures. The figure depicts the fold change of cortisol synthesis between untreated keratinocytes and those treated with ACTH, IL-1, and IGF-1.
FIG. 8(B) depicts the results of RT-PCR using untreated keratinocytes, or those treated with ACTH, IL-1, or IGF-1, and primers specific for CYP11B.

IL-1 Induces, and IGF-1 Inhibits, Cortisol Synthesis and CYP11B1 Expression To determine if injury-related molecules affect cortisol synthesis, IL-1 or IGF-1 was added to keratinocytes cultured as described in Example 1(C) or skin explants. IL-1 is a primary injury-response pro-inflammatory signal whereas IGF-1 is known to modulate glucocorticoid metabolism (Rappolee et al. (1988) *Science* 241:708-12). ACTH was used as a positive control. Cortisol levels were measured 24 hours post-treatment using the ELISA assay described in Example 1(E). Significant induction of cortisol production was found in IL-1 treated cells and tissue, comparable to ACTH (FIG. 8(A)). In contract, IGF-1 inhibited cortisol production in both treated cells and tissue (FIG. 8(A)).

To elucidate the possible mechanism of regulation involved in these observations, the expression of CYP11B1 was measured using RT-PCR as described in Example 1(G). The expression levels of CYP11B1 corresponded to the cortisol production. IL-1 induced the expression of CYP11B1 similar to ACTH, whereas IGF-1 inhibited its expression (FIG. 8(B)). These data show that injury-related molecules control cortisol synthesis in epidermis by regulating the expression levels of enzymes that participate in the synthesis.

Example 9

Glucocorticoid Inhibits Epithelialization and Metyrapone Promotes Epithelialization In the case of injury, keratinocytes must inform each other that the barrier has been broken and must be repaired, which occurs by release of pre-stored IL-1 (Horiuchi et al. (2004) *J. Dermatol. Science* 35:224-6; Freedberg et al. (2001) *J. Invest. Dermatol.* 116:633-640; Iglesias et al. (1998) *Oncogene* 17:1195-205). As response to their own signals, keratinocytes start migrating and proliferating. The release of IL-1 by keratinocytes demarcates the pro-inflammatory phase of wound healing. Epithelialization is an important component of wound healing, often used as its defining parameter (Brem et al. (2003) *Surg. Tech. Int.* 11:23-31). The process is governed by extra-cellular signals such as pro-inflammatory cytokines and growth factors (Freedberg et al. (2001) *J. Invest. Dermatol.* 116:633-640; Tomic-Canic et al. (1998) *J. Dermatol. Science* 17:167-181; Kupper (1990) *J. Invest. Dermatol.* 94:146 S-150S). To close the gap in the skin, keratinocytes must loosen adhesion to each other and to the basal lamina, and "grasp, hold and crawl" over the matrix of freshly deposited dermal fibroblasts. This is followed by keratinocyte proliferation and demarcates the proliferation phase of wound healing. Once the wound is epithelialized, it demarcates the remodeling phase.

Figure 9:
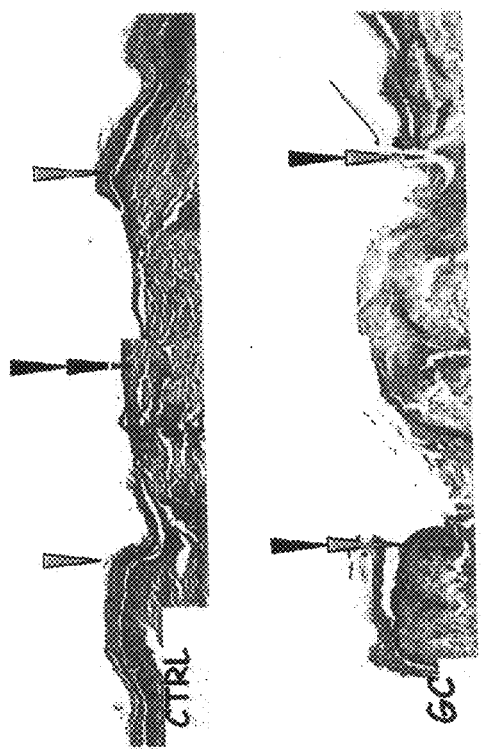
FIG. 9 shows the histology of the healing of untreated acute wound tissue and acute wound tissue treated with exogenous glucocorticoid.

The effect of glucocorticoids on epithelialization was tested using the acute wounding model described in Example 1(A). The wounded skin was maintained at the air-liquid interface for 6 days. Wounds were maintained in the presence or absence of clobetasol propionate (routinely used by dermatologists in the treatment of inflammatory skin disorders). Healing rates was determined by histology. Glucocorticoid or metyrapone was applied topically to the tissue. As shown by FIG. 9, the topical glucocorticoid treatment completely inhibited epithelialization while the untreated control wounds achieved complete closure. Thus, glucocorticoid inhibits epithelialization suggesting that glucocorticoid acts as a "stop" signal, i.e., a signal that resets the program from epithelialization to differentiation.

Figure 10:
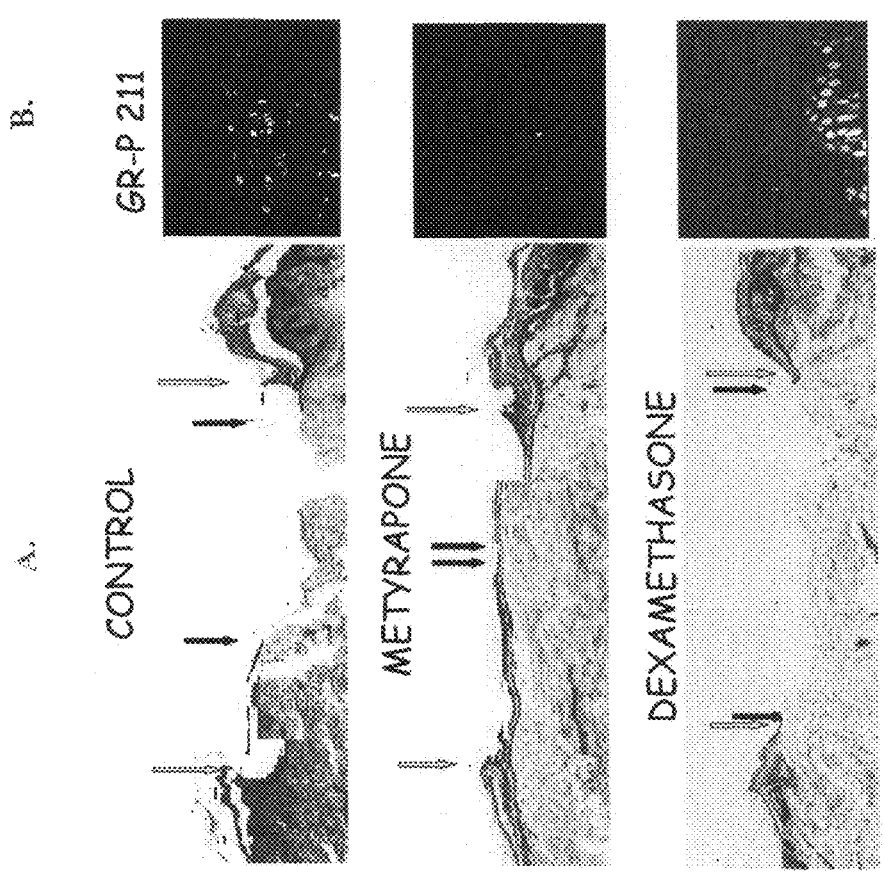
FIG. 10 shows the results of the effects of exogenous glucocorticoid and metyrapone on acute wound tissue.

Again using the acute wounding model described in Example 1(A), the effect of metyrapone, an inhibitor of endogenous glucocorticoid synthesis, on epithelialization was tested. 200 µM metyrapone was topically applied to the wounds. As shown in FIG. 10(A), complete wound closure was achieved in metyrapone treated skin in 6 days. Thus, it was concluded that metyrapone promotes epithelialization.

To confirm that metyrapone blocked hormone-activated GR by inhibiting cortisol synthesis, sections of the treated and untreated wound samples were stained with the anti-phospho-Ser211 antibody described in Example 1(B). In the metyrapone treated skin, there is an absence of GR in the nucleus, indicating that the activation of the glucocorticoid receptor is effectively blocked by metyrapone. In contrast, activated GR is found in the nucleus of the control and GC treated samples (FIG. 10(B)).

Example 10

Glucocorticoid Activates, and Metyrapone Inhibits, c-myc Expression in Epidermis and Keratinocytes It has been previously found that c-myc mRNA was induced by exogenous glucocorticoid (Stojadinovic et al.

(2007) *J. Biol. Chem.* 282:4021-34) whereas it was repressed in early phases of wound healing (Stojadinovic et al. (2005) *Am. J. Pathol.* 167:59-69). These data were confirmed by Northern Blot analysis of glucocorticoid treated keratinocytes (FIG. 11(A)). It was also found by Northern Blot analysis using acute wound tissue that c-myc was induced at 96 hours post-wounding (FIG. 11(B)).

Using Western Blot analysis, it was shown that protein levels of c-myc were induced by exogenous glucocorticoid and blocked by metyrapone (FIG. 11(C)).

These data strongly correlate with endogenous cortisol induction peaking at 48 hours post wounding, with expression of c-myc being induced 48 hours later.

Example 11

Metyrapone Reverses Nuclearization of β-Catenin

Figure 12:
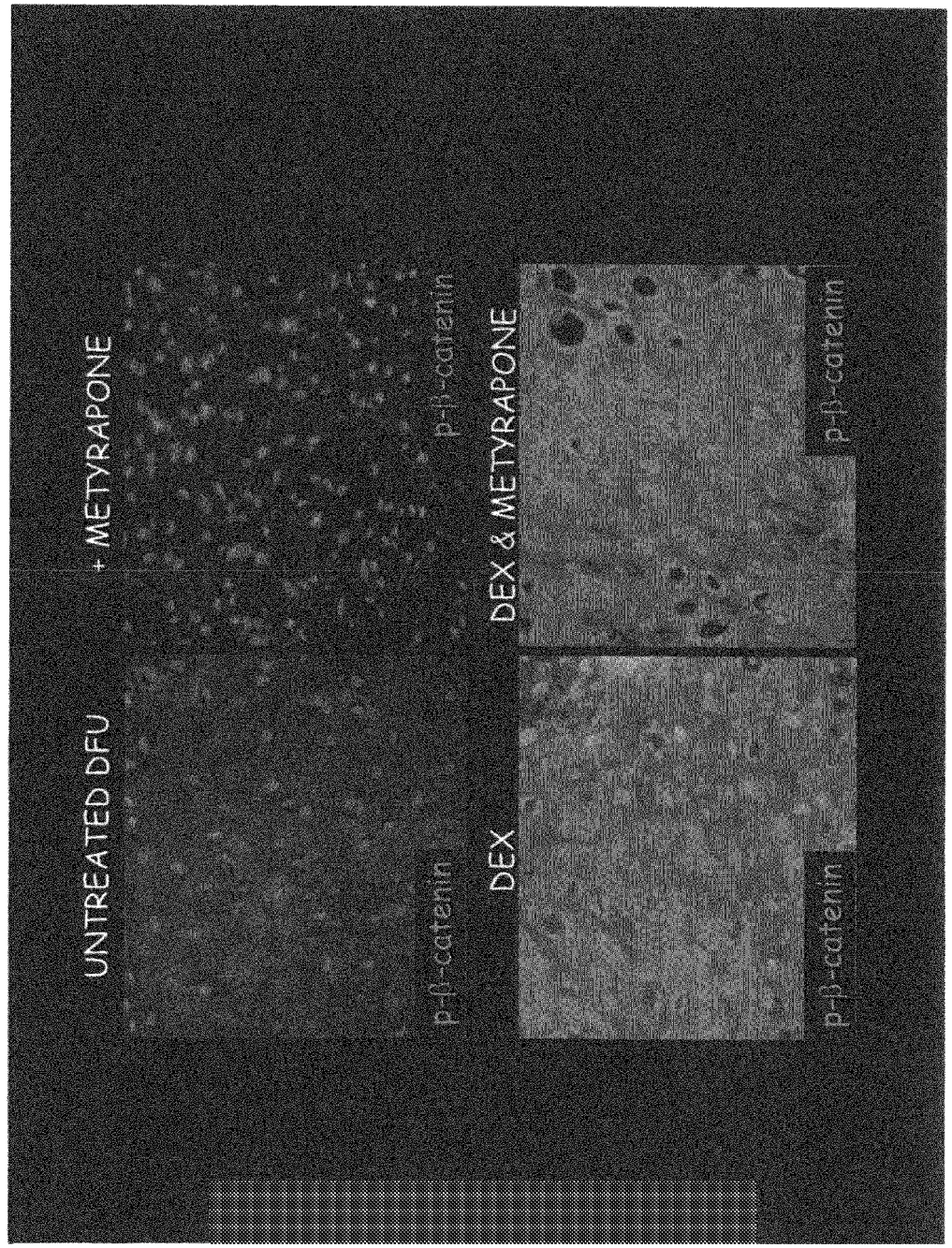
FIG. 12 shows the results of immunohistochemistry analysis of chronic wound tissue from a diabetic foot ulcer stained with an antibody targeting phosphorylated (activated) form of β-catenin, in untreated, glucocorticoid (dexamethasone) treated, metyrapone treated, and dexamethasone and metyrapone treated skin.

It has been previously reported that β-catenin and c-myc participate in inhibition of wound healing and contribute to the impairment of healing in chronic wounds. Specifically, it was found that the stabilization of β-catenin inhibits keratinocyte migration and wound healing in human skin culture and that β-catenin participates in GC signaling and repression of the keratin genes that participate in cytoskeletal network and keratinocyte migration. β-catenin, as well as c-myc, were found in the nonhealing edge of patients with chronic wounds (Stojadinovic et al. (2005) *Am. J. Pathol.* 167:59-69). To test if endogenous glucocorticoid participates in β-catenin activation in patients with chronic wounds, metyrapone was topically applied to chronic wound biopsies from patients with diabetic foot ulcers (as described in Example 1(A)). The effects were evaluated by measuring phosphorylation and intracellular translocation of β-catenin by immunohistochemistry as described in Example 1(B), except using an antibody targeting phosphorylated (activated) form of β-catenin (Cell Signaling Technology, Danvers, Mass.). As shown in FIG. 12, β-catenin phosphorylation and nuclearization typically found in chronic wounds was abolished by metyrapone. As also shown in FIG. 12, this effect can be reversed by the addition of an exogenous glucocorticoid.

From these data, it is shown that endogenous glucocorticoid participates in the activation of β-catenin in chronic wounds and further, that by inhibition of endogenous glucocorticoid synthesis, the pathogenic process can be reversed.

\* \* \*

The present invention is not limited in scope by specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method of inhibiting de novo glucocorticoid production in the epidermis in a subject in need of such treatment, wherein the subject has a wound of the skin, comprising applying a therapeutically effective amount of a composition comprising an antagonist of the steroid 11-beta-hydroxylase (CYP11B) enzyme to the epidermis of the subject, wherein the antagonist of CYP11B enzyme is metyrapone.

2. The method of claim 1, further comprising the application of a corticosteroid to the epidermis.

3. The method of claim 1, wherein the subject in need of treatment has an acute wound of the skin.

4. The method of claim 1, wherein the subject in need of treatment has a chronic non-healing wound of the skin.

\* \* \* \* \*

```
                           SEQUENCE LISTING

<160> NUMBER OF SEQ ID NOS: 2

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1
gctagacata ggggctcc                                                   18

<210> SEQ ID NO 2
<211> LENGTH: 18
<212> TYPE: DNA
<213> ORGANISM: Artificial
<220> FEATURE:
<223> OTHER INFORMATION: primer

<400> SEQUENCE: 2
aggtgtttca gcacatgg                                                   18
```